United States Patent
Scher et al.

(10) Patent No.: US 8,173,159 B2
(45) Date of Patent: *May 8, 2012

(54) MICROCAPSULES

(75) Inventors: Herbert Benson Scher, Moraga, CA (US); Jinling Chen, Randolph, NJ (US); Isabelle Mazeaud, San Francisco, CA (US); David Braun Kanne, Corte Madera, CA (US); Ian Malcolm Shirley, Bracknell (GB); Philip Wade, Runcorn (GB); John Christopher Padget, Frodsham (GB); Anne Waller, Wokingham (GB)

(73) Assignee: Syngenta Limited, Bracknell (GB)

( * ) Notice: Subject to any disclaimer, the term of this patent is extended or adjusted under 35 U.S.C. 154(b) by 90 days.

This patent is subject to a terminal disclaimer.

(21) Appl. No.: 09/873,418

(22) Filed: Jun. 5, 2001

(65) Prior Publication Data
US 2002/0136773 A1    Sep. 26, 2002

Related U.S. Application Data

(60) Provisional application No. 60/209,719, filed on Jun. 5, 2000, provisional application No. 60/209,734, filed on Jun. 5, 2000.

(51) Int. Cl.
*A61K 9/48* (2006.01)
*A61K 9/50* (2006.01)
*A61K 9/16* (2006.01)
*A01N 25/28* (2006.01)

(52) U.S. Cl. ......... 424/452; 424/497; 424/451; 504/359
(58) Field of Classification Search .................. 424/451, 424/497, 408, 489, 400, 452; 504/359
See application file for complete search history.

(56) References Cited

U.S. PATENT DOCUMENTS

| | | | |
|---|---|---|---|
| 4,285,720 A | 8/1981 | Scher | |
| 4,465,756 A * | 8/1984 | Mikami et al. | 430/138 |
| 4,956,129 A * | 9/1990 | Scher et al. | 264/4.7 |
| 5,160,529 A * | 11/1992 | Scher et al. | 424/408 |
| 5,332,584 A | 7/1994 | Scher et al. | |
| 5,925,464 A | 7/1999 | Mulqueen | |
| 5,925,595 A * | 7/1999 | Seitz et al. | 504/359 |
| 6,020,066 A | 2/2000 | Weisser et al. | |
| 6,022,501 A | 2/2000 | Dexter et al. | |
| 6,710,092 B2 * | 3/2004 | Scher et al. | 516/59 |
| 7,271,200 B2 * | 9/2007 | Scher et al. | 516/59 |

FOREIGN PATENT DOCUMENTS

| | | | |
|---|---|---|---|
| EP | 0823993 | 2/1998 | |
| WO | WO 00/05951 | * 2/2000 | |

* cited by examiner

*Primary Examiner* — Blessing Fubara
(74) *Attorney, Agent, or Firm* — William A. Teoli, Jr.

(57) ABSTRACT

A novel microcapsule comprising an encapsulated material which is enclosed within a solid permeable shell of a polymer resin having surface modifying compounds capable of reacting with isocyanate incorporated therein is disclosed. The process for producing such microcapsules is likewise disclosed.

12 Claims, 2 Drawing Sheets

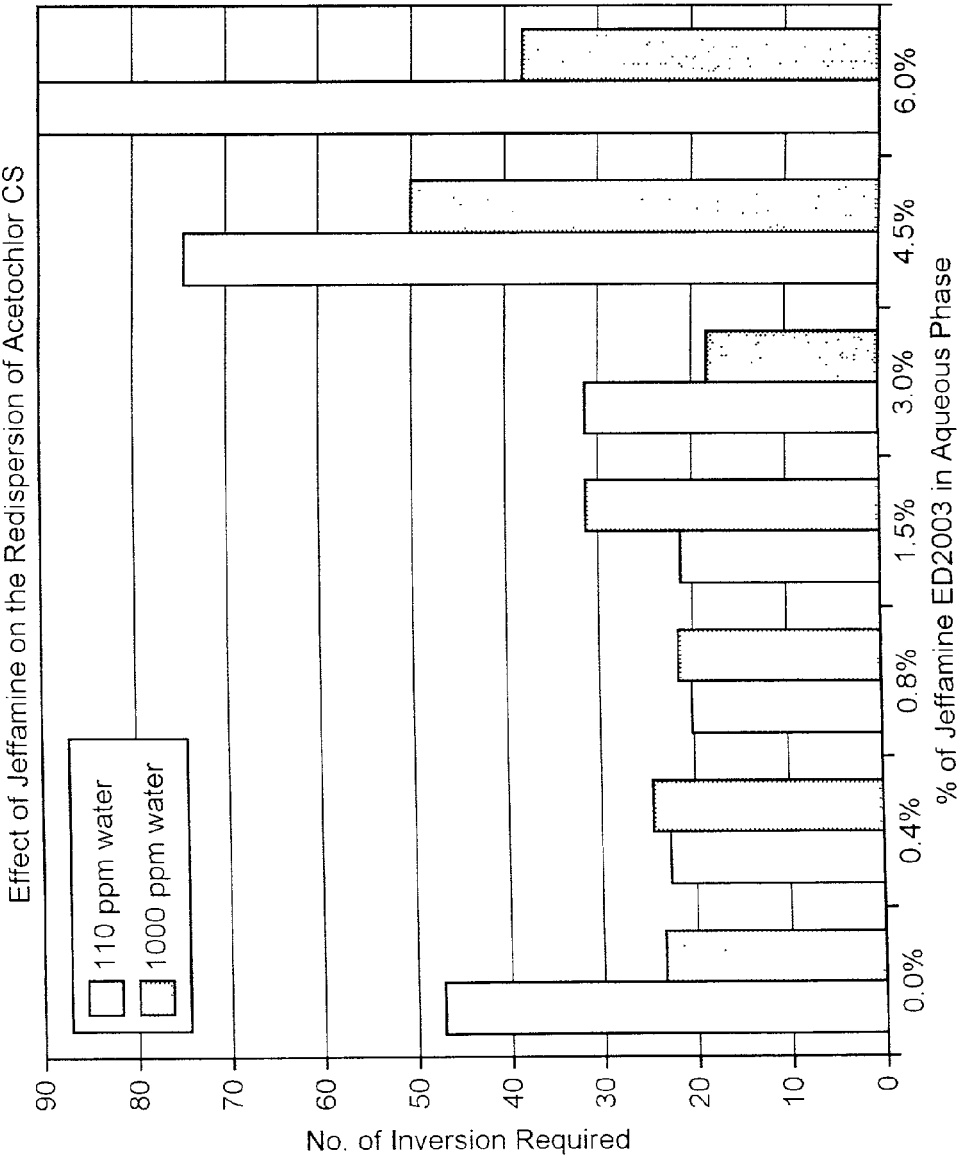

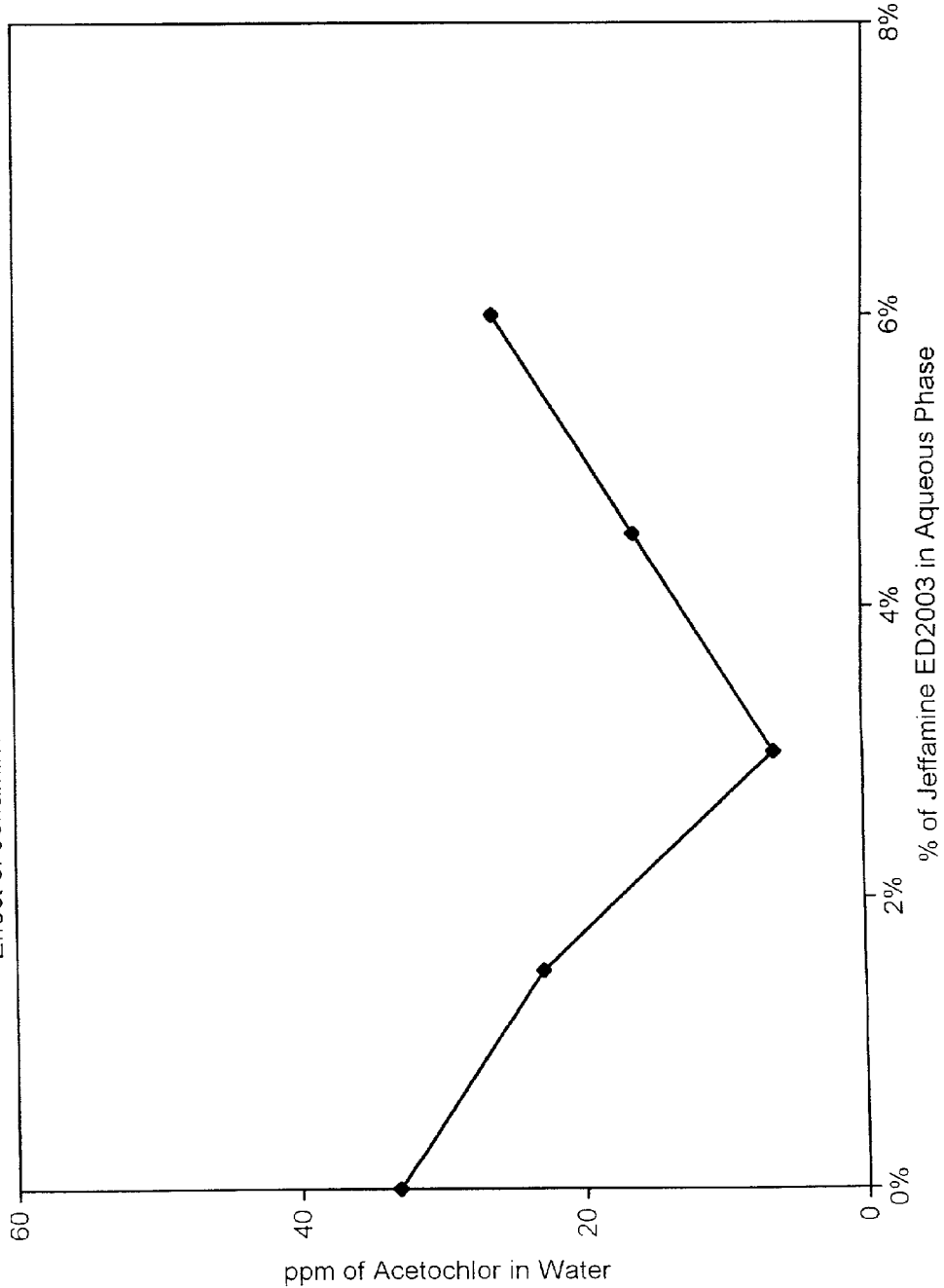

MICROCAPSULES

This application claims benefit of U.S. Provisional Application 60/209,719 filed Jun. 5, 2000 and U.S. Provisional Application 60/209,734 filed Jun. 5, 2000.

FIELD OF THE INVENTION

This invention relates to capsules of the nano and micron size (collectively, microcapsules) and to a process for their production. More particularly, this invention relates to encapsulated droplets of a liquid material that is substantially insoluble in water, and where the encapsulating shell has surface modifying compounds contained therein, thereby forming a modified capsule wall having a number of advantages. Further, this invention relates to the processes for the production of such capsules, including intermediate processes, and methods for their use.

BACKGROUND OF THE INVENTION

The use of microcapsules for both the slow or controlled and fast or quick release of liquid, solid and solids dissolved or suspended in solvent is well known in the chemical art, including the pharmaceutical, specialty chemical and agricultural industries. In agriculture, these release techniques have improved the efficiency of herbicides, insecticides, fumgicides, bactericides and fertilizers. Non-agricultural uses have included encapsulated dyes, inks, pharmaceuticals, flavoring agents and fragrances.

The material used in forming the wall of the microcapsule is typically taken from resin intermediates or monomers. The wall tends to be porous in nature, and may release the entrapped material to the surrounding medium at a slow or controlled rate by diffusion through the wall. The capsules may be alternatively designed so as to quickly release the material to the surrounding medium by modifying the crosslinkage in the wall. Further, the encapsulated material may be released in either a controlled or quick manner by means of a trigger mechanism built into the wall, wherein the trigger may be environmentally sensitive allowing quick breakdown of the wall under certain conditions. In addition to providing controlled or quick release, the walls also serve to facilitate the dispersion of water-immiscible liquids into water and water-containing media such as wet soil. Droplets encapsulated in this manner are particularly useful in agriculture.

Various processes for microencapsulating material have been previously developed. These processes can be divided into three broad categories—physical, phase separation and interfacial reaction methods. In the physical methods category, microcapsule wall material and core particles are physically brought together and the wall material flows around the core particle to form the microcapsule. In the phase separation category, microcapsules are formed by emulsifying or dispersing the core material in an immiscible continuous phase in which the wall material is dissolved and caused to physically separate from the continuous phase, such as by coacervation, and deposit around the core particles. In the interfacial reaction category, the core material is emulsified or dispersed in an immiscible continuous phase, and then an interfacial polymerization reaction is caused to take place at the surface of the core particles thereby forming microcapsules.

The above processes vary in utility. Physical methods, such as spray drying, spray chilling and humidized bed spray coating, have limited utility for the microencapsulation of products because of volatility losses and pollution control problems associated with evaporation of solvent or cooling, and because under most conditions not all of the product is encapsulated nor do all of the polymer particles contain product cores. Phase separation techniques suffer from process control and product loading limitations. It may be difficult to achieve reproducible phase separation conditions, and it may be difficult to ensure that the phase-separated polymer will preferentially wet the core droplets.

Interfacial polymerization reaction methods have proven to be the most suitable processes for use in the agricultural industry for the microencapsulation of pesticides. There are various types of interfacial reaction techniques. In one type of interfacial condensation polymerization microencapsulation process, monomers from the oil and aqueous phases respectively are brought together at the oil/water interface where they react by condensation to form the microcapsule wall ("two phase polymerisation"). In general such reactions involve the condensation of an isocyanate moiety on one monomer with a second moiety such as an amine on a second monomer.

In another type of polymerization reaction, the in situ interfacial condensation polymerization reaction, all of the wall-forming monomers or pre-polymers are contained in one phase (the oil phase or the aqueous phase as the case may be). In one process the oil is dispersed into a continuous or aqueous phase solution comprising water and a surface-active agent. The organic phase is dispersed as discrete droplets throughout the aqueous phase by means of emulsification, with an interface between the discrete organic phase droplets and the surrounding continuous aqueous phase solution being formed. In situ condensation of the wall-forming materials and curing of the polymers at the organic-aqueous phase interface may be initiated by heating the emulsion to a temperature between of about 20° C. to about 85° C. and optionally adjusting the pH. The heating occurs for a sufficient period of time to allow substantial completion of in situ condensation of the monomers or pre-polymers to convert the organic droplets to capsules consisting of solid permeable polymer shells enclosing the organic core materials.

Many such in situ condensations involve isocyanate moieties. For example one type of microcapsule prepared by in situ condensation and found in the art, as exemplified in U.S. Pat. No. 4,285,720 is a polyurea microcapsule which involves the use of at least one polyisocyanate such as polymethylene polyphenyleneisocyanate (PMPPI) and/or tolylene diisocyanate (TDI) as the wall-forming material. In the creation of polyurea microcapsules, the wall-forming reaction is initiated by heating the emulsion to an elevated temperature at which point the isocyanate groups are hydrolyzed at the interface to form amines, which in turn react with unhydrolyzed isocyanate groups to form the polyurea microcapsule wall.

Isocyanates may undergo many types of chemical transformations such as homopolymerisation, oligomerisation, cycloaddition, insertion and nucleophilic reactions as described in the text H. Ulrich, CHEMISTRY AND TECHNOLOGY OF ISOCYANATES, John Wiley & Sons, Chichester, United Kingdom (1996). In the context of microcapsule wall formation, nucleophilic reactions are the most important. Typical nucleophiles include carboxyl, thiol, active methylene, hydroxyl and amino groups.

The use of isocyanates in which the —NCO group is 'masked' is well known in isocyanate polymer chemistry. For example, the —NCO group may be reacted with various molecules (BH) to give blocked isocyanates (RNHCOB) as described in Wicks & Wicks, PROGRESS IN ORGANIC COATINGS, Vol. 36, pp. 148-72 (1999). The blocked isocyanates may be de-blocked by further reaction with nucleophiles:

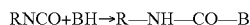

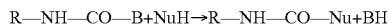

While we do not exclude the use of blocked isocyanates in the present invention, that approach is not preferred as it normally requires relatively high (>100° C.) temperatures for the deblocking reaction, and as the blocking agents are released into the medium.

A further type of microcapsule prepared by in situ condensation which does not involve the reaction of isocyanate groups is exemplified in U.S. Pat. Nos. 4,956,129 and 5,332,584. These microcapsules, commonly termed "aminoplast" microcapsules, are prepared by the self-condensation of etherified urea-formaldehyde resins or prepolymers in which from about 50 to about 98% of the methylol groups have been etherified with a $C_4$-$C_{10}$ alcohol (preferably n-butanol). The prepolymer is added to or included in the organic phase of an oil/water emulsion. Self-condensation of the prepolymer takes place under the action of heat at low pH. To form the microcapsules, the temperature of the two-phase emulsion is raised to a value of from about 20° C. to about 90° C., preferably from about 40° C. to about 90° C., most preferably from about 40° C. to about 60° C. Depending on the system, the pH value may be adjusted to an appropriate level. For the purpose of this invention a pH of about 1.5 to 3 is appropriate.

Microcapsules produced by such in situ condensation have the benefits of high pesticide loading and low manufacturing costs, as well as a very efficient membrane and no reactive residue remaining in the aqueous phase.

Regardless of the type of process utilized, the final encapsulated products may be packaged and used in a number of forms. For instance, they may be used in the form of a suspension of microcapsules in a liquid such as water or another aqueous medium (generally termed a suspension concentrate). Alternatively they may be packaged and used as dried microcapsules (for instance, produced from suspensions of microcapsules in liquids by techniques such as by spray drying, flat plate drying, drum drying or other drying methods). In yet a third way, they may be combined into other solid formulations such as granules, tapes or tablets containing microcapsules. All of these types of formulations are generally used by adding them to a liquid medium (usually water) in equipment such as a spray tank for agricultural use. Liquid media, whether that packaged with the microcapsules in suspension concentrate form, or that used in a spray tank or other application equipment, often has various ingredients in addition to water, including wetters, dispersants, emulsifiers, protective colloids or colloid stabilizers and surface active agents or surfactants. The protective colloids are used in processes for the preparation of the microcapsules and serve to prevent agglomeration of the oil droplets prior to encapsulation, or of the capsules after wall formation, as well as aiding the redispersing of the capsules upon settling. The surfactants perform various functions depending upon the type of surfactant used. These include varying the permeability of the wall, aiding in dispersing the capsules, acting as a wetter, reducing or eliminating foaming, affecting the adhesiveness of the capsule to the surface to which it is applied, and so forth. Primarily, the surfactants act as free, non-bound emulsifiers in the preparation of the precursor emulsion. However, under certain conditions the protective colloids, surfactants and emulsifiers can become desorbed or otherwise separated (to varying degrees) from the microcapsules so that they do not continue to perform their functions as effectively.

SUMMARY OF THE INVENTION

It has been discovered that one or more wall-modifying compounds (termed "surface-modifying agents") can, by virtue of reaction with the wall-forming materials, be incorporated in the microcapsule wall to create a modified microcapsule surface with built-in surfactant and/or colloid stabilizing properties. The preferred compounds in this invention have weak or nonexistent surface activity and/or colloid stabilizing properties in and of themselves but contain within the molecular structure one or more moieties that are capable of imparting surface activity.

PRIOR ART

U.S. Pat. No 6,022,501 (assigned to American Cyanamid Company) discloses pH-sensitive microcapsules obtained by introducing a polyacid halide into the emulsion during the formation of a polyamide, polyester, polyamide/polyester or cross-linked amino resin microcapsule wall such that free carboxylic acid groups are incorporated in the shell wall. Such microcapsules are stable at pH values from about pH 1 to pH 5.5 and release their contents at pH values greater than about 5.5.

U.S. Pat. No. 5,925,464 (assigned to Dow AgroSciences) discloses a method of encapsulating pesticidal materials, in which microcapsules containing the active material are formed by means of an interfacial polycondensation reaction, involving an isocyanate/polyamine reaction in the presence of a polyvinyl alcohol ("PVA"). This reference mentions that the PVA, having pendant —OH groups, reacts with the isocyanate to incorporate polyurethane groups into the polymeric microcapsule walls.

U.S. Pat. No. 6,020,066 (assigned to Bayer AG) discloses a process for forming microcapsules having walls of polyureas and polyiminoureas, wherein the walls are characterized in that they consist of reaction products of crosslinking agents containing $NH_2$ groups with isocyanates. The crosslinking agents necessary for wall formation include di- or polyamines, diols, polyols, polyfunctional amino alcohols, guanidine, guanidine salts, and compounds derived therefrom. These agents are capable of reacting with the isocyanate groups at the phase interface in order to form the wall.

BRIEF DESCRIPTION OF THE DRAWINGS

FIG. 1 generally illustrates the effect upon redispersibility of wall-modified microcapsules.

FIG. 2 generally illustrates the effect upon permeability, or release rate, of wall-modified microcapsules.

DETAILED DESCRIPTION OF THE INVENTION

It has been found that, by use of the concepts of this invention in the above-mentioned conventional microcapsule processes, it is possible to produce a modified chemical structure that alters the properties of the capsule. The process employs surface modifying compounds that generally exhibit little or no type of surface activity, but contain one or more moieties that are capable of imparting surface activity when the compound is chemically attached to the microcapsule wall. Thus, when such compounds are incorporated into the wall of the capsules, capsules with enhanced properties are formed.

In its simplest form, the microcapsule of the present invention is comprised of a core material encapsulated by a wall formed from one or more monomer or oligomer or polymer compounds, wherein the wall has been modified to incorporate one or more agents which affect the properties of the capsule.

Thus according to the present invention there is provided a microcapsule comprising an encapsulated material enclosed within a solid permeable shell of a polymer resin wherein the polymer resin has incorporated therein at least one surface modifying compound wherein said surface modifying compound is selected from compounds having a formula (I), (II), (III) (IV) or (V)

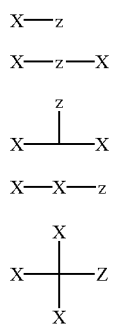

wherein Z is a moiety that contributes to modifying the surface properties of said microcapsule and each X is, independently, a functional moiety capable of reacting with a wall-forming material and the moieties designated by lines linking the X and Z functional groups have a molecular weight of between 50 and 4000, and may be optionally substituted aryl, hydrocarbyl, or heterocyclic units, or combinations thereof, optionally containing internally linked amino, ether, thioether, acetal, ester, thioester, amide, sulphonamide, urethane, urea, carbonate, siloxane, or phosphonamide groups or combinations thereof.

Preferably —X is hydroxyl, thiol, amino or carboxylate. When X is amino it is preferably a group —NHA wherein A is hydrogen or $C_1$ to $C_4$ alkyl. When X is carboxylate it is suitably a group —CO—OR where R is hydrogen or a hydrocarbyl moiety having 1-30 carbon atoms optionally linked or substituted by one or more halo, amino, ether or thioether groups or combinations of these. It is preferred that R is hydrogen for isocyanate wall-forming systems. For aminoplast wall-forming systems, R is preferably hydrogen or $C_1$ to $C_{12}$ straight or branched chain alkyl. In structure (IV) above, the group —X— should be capable of undergoing reaction with the wall-forming material and is preferably an amino linking group —NH. Where more than one moiety —X is present, the respective groups X may be the same or different.

The surface modifying compounds of the present invention contain one or more functional groups (designated Z) capable of imparting surface activity at the surface of the microcapsule. The nature of the group Z is such that it interacts strongly with the continuous aqueous phase in the process for preparation of the microcapsules, for oil-in-water systems, which are the preferred systems of this invention. However, the invention is also useful in connection with water-in-oil systems; there the group Z must interact strongly with the organic continuous phase. Z may be charged or non-charged, but in the context of the present invention, is hydrophilic in nature for oil-in-water systems. Preferably —Z comprises sulphonate, carboxylate, phosphonate, phosphate, quaternary ammonium, betaine, oxyethylene or an oxyethylene-containing polymer. When —Z is sulphonate, carboxylate, phosphonate or phosphate it may be in the form of the free acid but is preferably present in the form of a salt (i.e. —Z⁻ anion), for example an alkali metal salt. When —Z is quaternary ammonium (as that expression is used herein) it suitably has the structure

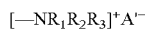

wherein $R_1$, $R_2$ and $R_3$ are independently hydrogen or $C_1$ to $C_4$ alkyl and $A'^-$ is a suitable inorganic or organic anion such as halide or acetate. Preferably not more than one of R is hydrogen It will be appreciated that when —Z is a positively or negatively charged species it may be converted from a charged species to a non-ionised form and visa versa, depending on the pH. Thus for example it may be convenient to incorporate a molecule containing the group —Z in non-ionised form and then convert it into an ionised form subsequently.

When —Z is oxyethylene or an oxyethylene-containing polymer, it is preferably an oxyethylene polymer or a random or block oxyethylene/oxypropylene copolymer, preferably containing an oxyethylene to oxypropylene ratio of grater than 1. Typically therefore Z may take the form

wherein $R_4$ is an end-capping group such as $C_1$ to $C_4$ alkyl, especially methyl, r, and s are independently from 0 to 3000 or more preferably 0 to 2000, provided that s is not 0 and the total of r+s is from about 7 to about 3000 or more preferably from about 10 to about 2000 and EO and PO represent oxyethylene and oxypropylene respectively which may be arranged in random or block formation. Preferably, r and s are independently from 0 to 100, provided that the total of r+s is from about 10 to about 100. It is especially preferred that r and s are independently from 0 to 25 and the total for r+s is from 10 to 25. Preferably s is greater than r, for example s is preferably at least 4 times greater than r. When —Z represents an ethylene oxide—propylene oxide block copolymer, it may have the structure

wherein $R_4'$ is an end-capping group such as $C_1$ to $C_4$ alkyl, especially methyl, r', s' and t are independently from 0 to 2000, provided that s' is not 0 and the total of r'+s'+t is from about 7 to about 3000 or more preferably from about 10 to about 2000 and EO and PO represent oxyethylene and oxypropylene respectively. Preferably s' is greater than the sum of r'+t, for example it is preferred that s' is at least 4 times greater than the sum of r'+t. Preferably r', s' and t are independently from 0 to 100, provided that the total of r'+s'+t is from about 10 to about 100.

When Z has the structure —Z— in formula (II) above it is suitably an oxyethylene-containing polymer having the formula as shown in (IIA) below.

It is preferred that X and Z are not both carboxylate at the same time.

It will be appreciated that if X and Z are groups which are capable of reacting together, for example carboxylate and/or sulphonate, X and Z may together form a ring structure capable of ring opening under the conditions of the wall-modifying reaction The moieties linking the X and Z functional groups have a molecular weight of between 50 and 4000, and may be optionally substituted aryl, hydrocarbyl, or heterocyclic units, or any combination thereof, optionally containing internally linked amino, ether, thioether, acetal, ester, thioester, amide, sulphonamide, urethane, urea, carbonate, siloxane, or phosphonamide groups or combinations of these. Certain ether groups such as —CCH$_3$CH$_2$O— units are known to promote the solubility of the modifying molecule in the oil phase. When more than one functional group X is present, the groups may be separated by from 2 to 400 atoms, and more preferably from 2 to 150 atoms.

The moieties linking the X and Z functional groups have a preferred molecular weight of between 70 and 2000 and more particularly typically comprise, singly or in combination:
- one or more straight or branched aliphatic chains having a total of 1-400 carbon atoms, preferably 2-200 carbon atoms and more preferably 2-100 carbon atoms optionally containing one or more saturated or unsaturated aliphatic or aromatic carbocyclic groups having 3-14 carbon atoms in the ring(s) wherein the aliphatic or carbocyclic carbons are optionally internally linked or substituted by one or more halo, amino, ether, thioether, acetal, ester, thioester, amide, sulphonamide, urethane, urea, carbonate, siloxane, or phosphonamide groups or combinations of these. Illustrative examples of ring structures which are optionally present include phenyl, naphthyl, cylopentyl, cyclohexyl, and the like.
- one or more alkenyl or alkynyl groups optionally linked or substituted by one or more alkyl, halo, amino, ether, thioether, acetal, ester, thioester, amide, sulphonamide, urethane, urea, carbonate, siloxane, or phosphonamide groups or combinations of these.
- one or more heterocyclic groups having a ring size of from 4-10 atoms and containing 1-3 heteroatoms selected independently from nitrogen, oxygen, sulphur, sulphone or sulphoxide (such as tetrahydrofiryl, pyridyl, and the like) and optionally linked or substituted by one or more alkyl, halo, amino, ether, thioether, acetal, ester, thioester, amide, sulphonamide, urethane, urea, carbonate, siloxane, or phosphonamide groups or combinations of these.
- one or more saturated or unsaturated aliphatic or aromatic carbocyclic groups having 3-14 carbon atoms in the ring(s) wherein the aliphatic or carbocyclic carbons are optionally internally linked or substituted by one or more halo, amino, ether, thioether, acetal, ester, thioester, amide, sulphonamide, urethane, urea, carbonate, siloxane, or phosphonamide groups or combinations of these. Illustrative examples of ring structures include phenyl, naphthyl, cyclopentyl, cyclohexyl, and the like.

The alkyl groups that are optional substituents typically have 1-8, 1-6, 1-4, or 1-3 carbon atoms, such as methyl, ethyl, propyl, and the like.

The nature of Z and/or of the moieties linking the X and Z functional groups affects (i) the solubility of the surface modifying compound in the discontinuous oil phase and its differential solubility between the continuous aqueous phase and the discontinuous oil phase to be encapsulated, (ii) the process of choice, and/or (iii) the properties of the modified capsule as will be discussed in greater detail below.

The moieties linking the X and Z functional groups in the generalized structures (I) to (IV) above are illustrated by but are not limited to surface modifying compounds as follows.

A preferred structure (I) has the formula

    X—Y$_1$—Z    (IA)

wherein Y$_1$ represents the moiety linking X and Z (the lines representing bonds in this instance) and —X and —Z are as hereinbefore defined.

In formula (IA) Y$_1$ can be any of the linking groups listed above for the moiety linking X and Z but is preferably a straight or branched chain alkyl linking group containing from 1 to 20 carbon atoms and preferably from 2 to 10 carbon atoms; or is phenyl, naphthyl, cyclopentyl or cyclohexyl; or when Z is an oxyethylene or an oxyethylene-containing polymer, Y$_1$ preferably represents a direct link between X and Z Structure (IA), wherein Z is an oxyethylene containing polymer thus has the formula,

    R$_4$—O(PO)$_r$(EO)$_s$—X    (IB)

wherein R$_4'$, r', s' and t are as defined in relation to formula (VI) above. When —Z is a block copolymer, structure (IA) has the formula

    R$_4'$—O(PO)$_r$(EO)$_s$(PO)$_t$—X    (IC)

wherein R$_4'$, r', s' and t are as defined in relation to formula (VII) above. An example of a compound of formula (IA) wherein X is —OH is methoxy-polyethylene glycol of molecular weights from 350 to 2000 [MeO(EO)$_n$OH]. A further example of a compound of formula (IA) wherein X is amino is JEFFAMINE XTJ-508 [MeO(EO)$_n$(PO)$_m$NH$_2$] wherein n is 32 and m is 10. The molecular weight is 2000. (JEFFAMINE is a trademark of Huntsman).

Examples of compounds of formula (IA) in which Y$_1$ is a an alkyl linking group include taurine sodium salt [H$_2$NCH$_2$CH$_2$SO$_3$Na], 2-mercaptoethanesulphonic acid [HSCH$_2$CH$_2$SO$_3$H], 2-(dimethylamino)-ethanethiol hydrochloride [(CH$_3$)$_2$N$^+$(H)CH$_2$CH$_2$SH]Cl$^-$ and 3-mercaptopropionic acid [HSCH$_2$CH$_2$CO$_2$H] and salts thereof.

When Y$_1$ is a ring structure group such as an aryl group, the substituents X and Z in formula (IA) may be direct substituents in the ring for example:

(ID)

If X and Z are adjacent substituents capable of reacting together such as carboxyate and/or sulphonate they may form a cyclic anhydride capable of ring-opening under the reaction conditions. An example of such a compound is 2-sulphobenzoic acid anhydride.

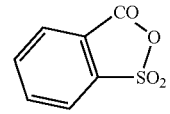

In structure (II) where two groups X are at distal ends of the molecule, —Z— may be an oxyethylene containing polymer and there is a direct bond between —Z— and each —X. Thus one preferred structure (II) has the formula:

    X-(EO)$_a$(PO)$_b$-X'    (IIA)

wherein a and b are independently from 0 to 3000 or more preferably from 0 to 2000, provided that a is not 0 and the total of a+b is from about 7 to about 3000 or more preferably from about 10 to about 2000 and EO and PO represent oxyethylene and oxypropylene respectively which may be arranged in random or block formation. More preferably, a and b are independently from 0 to 200, provided that the total of a+b is from about 10 to about 200. Preferably a is greater than b, for example it is preferred that a is at least 4 times greater than b. When —Z— represents an ethylene oxide, propylene oxide block copolymer, the compound may have the structure

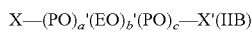

X—(PO)$_a$'(EO)$_b$'(PO)$_c$—X' (IIB)

wherein a', b' and c are independently from 0 to 2000, provided that b' is not 0 and the total of a'+b'+c is from about 7 to about 3000 or more preferably from about 10 to about 2000 and EO and PO represent oxyethylene and oxypropylene respectively. Preferably b' is greater than the sum of a'+c, for example at least 4 times greater than the sum of a'+c. Preferably a', b' and c are independently from 0 to 200, provided that the total of a'+b'+c is from about 10 to about 200. The groups X and X' may be the same or different but are conveniently the same. An example of a compound of formula (IIB) wherein the terminal —OH groups are replaced by —NH$_2$ is JEFFAMINE ED2003 [H$_2$NCHMeCH$_2$—(PO)$_a$-(EO)$_b$—(PO)$_a$—NH$_2$], where a+c=2.5 and b=41, available from Huntsman.

Alternatively —Z— in structure (II) may be quaternary ammonium. Thus for example a further preferred structure (II) has the formula (IIC)

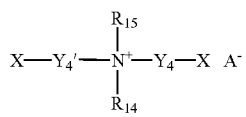

(IIC)

wherein R$_{14}$ and R$_{15}$, which may be the same or different are hydrogen C$_1$ to C$_{20}$ straight or branched chain alkyl; aryl for example phenyl; or C$_1$ to C$_4$ aralkyl, for example benzyl, wherein each aryl group may be optionally substituted by conventional substituents such as C$_1$ to C$_4$ alkyl, nitro and halo and wherein Y4 and Y4' which may be the same or different are

—R$_8$—

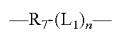

—R$_7$-(L$_1$)$_n$— wherein R$_7$, and R$_8$ are independently C$_1$ to C$_{10}$ straight or branched chain alkyl linking groups optionally substituted by halogen or ether, for example C$_1$ to C$_4$ alkoxy and (L$_1$)$_n$ is a polyoxyalkyene group such as polyoxyethylene or more preferably polyoxypropylene or polyoxybutylene; n is from 2 to 20, preferably from 4 to 10 and A— is a suitable anion.

It is preferred that both R$_{14}$ and R$_{15}$ are not hydrogen at the same time. An example of a surface modifying compound of formula (IIC) is a benzoxonium chloride such as that illustrated in Example 18 or an amino oxyethylene diol such as that illustrated in Example 19.

Structure (III), where two X groups are at distal ends of the molecule and Z is a pendant group, may in one embodiment take the form:

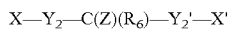

X—Y$_2$—C(Z)(R$_6$)—Y$_2$'—X' (IIIA)

wherein R$_6$ is hydrogen or more preferably a C$_1$ to C$_4$ alkyl group optionally substituted by ether, for example C$_1$ to C$_4$ alkoxy or halogen and Y$_2$ and Y$_2$', which may be same or different are independently

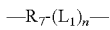

—R$_7$-(L$_1$)$_n$— or

—R$_8$— wherein R$_7$, and R$_8$ are independently C$_1$ to C$_{10}$ straight or branched chain alkyl linking groups optionally substituted by halogen or ether, for example C$_1$ to C$_4$ alkoxy and (L$_1$)$_n$ is a polyoxyalkyene group such as polyoxyethylene or more preferably polyoxypropylene or polyoxybutylene; n is from 2 to 20, preferably from 4 to 10.

Compounds of formula (IIIA) are illustrated by (i) the propoxylated derivative of 1,4-butanediol-3-sodiosulphonate (ii) dimethylolpropionic acid ("DMPA") and (iii) dimethylol butyric acid ("DMBA")

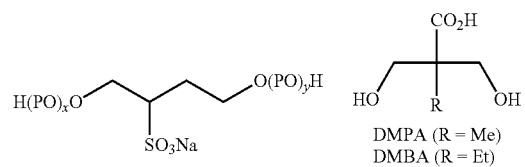

DMPA (R = Me)
DMBA (R = Et)

When the moiety linking X and Z is a ring structure group such as an aryl group, the substituents X and Z in formula (III) may be direct substituents in the ring for example:

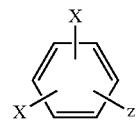

(IIIB)

An example of a compound of structure (IIIB) is illustrated by esters of 5-sodiosulphoisophthalate (SSIPA) where the groups R$_5$, which may be the same or different, are a hydrocarbyl moiety having 1-30 carbon atoms optionally linked or substituted by one or more halo, amino, ether or thioether groups or combinations of these. Preferably R$_5$ is a C$_6$ to C$_{20}$ straight or branched chain alkyl group.

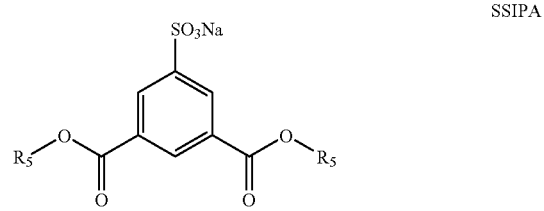

SSIPA

Alternatively the groups X and Z may be joined to the ring structure via linking groups, for example the compound of structure (III) may have the formula (IIIC):

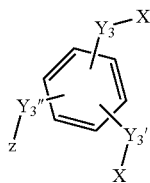

IIIC wherein $Y_3$, $Y_3'$ and $Y_3''$ may individually represent a direct link between X or Z (as the case may be) and the ring structure or may represent one of the linking groups described above. In particular, $Y_3$, $Y_3'$ and $Y_3''$ may independently have the definitions for $Y_2$ given above. Alternatively $Y_3$, $Y_3'$ and $Y_3''$ may independently be a group

where $L_2$ is an ester linking group —C(O)—O, $R_9$ is an oxyethylene, oxypropylene or oxybutylene group or polyoxyethylene, polyoxypropylene or polyoxybutylene group having a degree of polymerisation from 2 to 20. In one embodiment $Y_3''$ represents a direct link between Z and the aryl ring and —$Y_3$— and —$Y_3'$— are both -($L_2$)—$R_9$— as herein defined wherein $R_9$ is oxyethylene and X is —OH. An example of a compound of formula IIIC is (iv) bis(2-hydroxyethyl)-5-soidiosulphoisophthalate ("EG-SSIPA").

EG-SSIPA

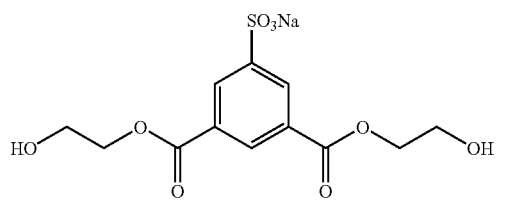

A further preferred class of compound of structure III has the formula IIID:

IIID

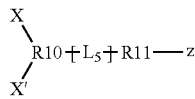

wherein R10 is a $C_1$ to $C_8$ straight or branched chain alkyl group and the two groups X and X', which may be the same or different, may be attached to the same carbon atom in the alkyl chain or to different carbon atoms in the alkyl chain, -$L_5$- a linking group which is

or

wherein $R_8$, and $(L_1)_n$ are as defined above in relation to formula IIIA and $R_{11}$ is $C_1$ to $C_4$ alkyl. As an example of a compound of formula (IIID), there may be mentioned Tegomer DS3117, a sulphonated diol supplied by Goldschmidt.

Tegomer DS3117

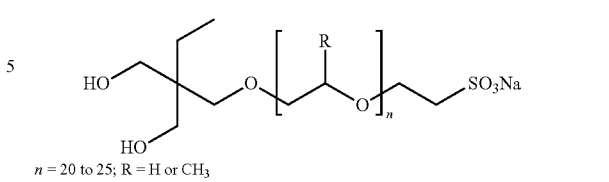

n = 20 to 25; R = H or $CH_3$

In structure (IV), the group —X— is both a linking group and is capable of reacting with the wall-forming material. It is preferred that the group —X— in structure (IV) is —NH—. Thus a general formula for a compound of structure (IV) is (IVA):

$$X—Y—NH—Y'—Z \qquad (IVA)$$

wherein Y and Y' may be any of the linking moieties described above or, when Z is an oxyethylene containing polymer may represent a direct link between Z— and —NH—. It will be appreciated that the reactivity of the groups —X and —NH— respectively with the wall-forming material will not necessarily be the same and, depending on the groups concerned, the primary reaction with the wall-forming material may be either via the terminal group —X or via the group —NH—. In some circumstances there may be no reaction between a group —NH— and the wall-forming material and in such a case, the group —NH— should not be regarded as a group —X— but rather as an internal amino linking group in the moiety joining X and Z. Preferred structures of Y and Y' include independently a straight or branched chain $C_1$ to $C_{10}$ alkyl group, a polyoxyethylene, or more preferably polyoxypropylene or polyoxybutylene polymer chain of formula -$(L_1)_n$- as defined above or a group -($L_2$)—$R_9$— as defined above or a group —$R_{12}$-($L_2$)—$R_9$— wherein $R_9$ and $L_2$ are as defined above and $R_{12}$ is a $C_1$ to $C_4$ alkyl group. Compounds of formula (IVA) are represented for example by Raschig Poly-EPS 520-Na

(i) PolyEPS 520 available from Raschig wherein —Y— is polyoxypropylene and Y' is a $C_3$ alkyl group, (ii) the Michael adduct of Jeffamine 1000M (available from Huntsman) and ethylhydroxyethylacrylate wherein Z is a methyl-capped polyoxyethylene-containing polymer linked directly to —NH— and Y' is a group —$R_{12}$-($L_2$)—$R_9$— as defined above in which $R_9$ is oxyethylene [MeO$EO_n$P$O_m$NHCH$_2$CH$_2$COOCH$_2$CH$_2$OH where n is about 18 and m is about 3] (iii) the ethoxylated adduct of Jeffamine M1000 wherein Z is a methyl-capped polyoxyethylene-containing polymer linked directly to —NH— and Y is a polyoxyethylene group [MeO$EO_n$P$O_m$NH(CH$_2$CH$_2$O)$_n$H].

Structure (V) is illustrated by the sulfonate polyester polyol prepared by reacting sodium sulphoisophthalic acid, adipic acid, cyclohexane dimethanol, methoxy-polyethylene glycol (mw 750) and trimethylol propane to give a product having a hydoxyl number in the range of from 150 to 170. There may be a variation in the structural composition of the product depending on the conditions used. It will be appreciated by those skilled in the art that the reaction will produce a complex mixture of molecules and the structure (V) should not therefore be taken as an exact representation of the sulphonate polyester polyol. Typically however the sulphonate polyester polyol will have at least two terminal —OH groups whilst the sulphonate group provides the —Z group. Structural variations however may mean that the number of moieties —X are average rather than absolute or an exact integer and in particular on average there may not be exactly three —X groups.

The polymer wall materials of this invention may be any polymer system conventionally used in microcapsule wall-formation or suitable for such use. Examples include wall materials made by a wide variety of isocyanate polymerisation reactions forming for example polyurea and polyurethane resins, non-isocyanate systems such as polyester, polythioester, polyamide polysulfonamide, polyphosphonamide, polycarbonate and polysiloxane polymers, and the self-condensation of an optionally etherified urea-formaldehyde prepolymer.

The use of such polymer resins as wall-forming materials in the manufacture of microcapsules will be familiar to those skilled in the art but the reactions involved may be conveniently summarised as follows wherein the structures in parenthesis illustrate a short-hand notation for the functional groups produced on polymerisation and are not polymeric structures in themselves:

Oil Phase    Continuous Phase (1)

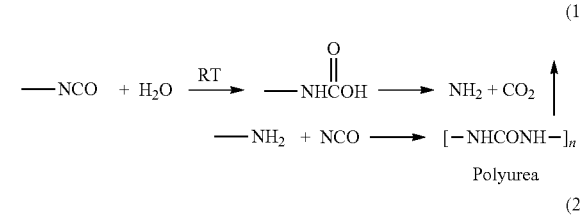
Polyurea (2)

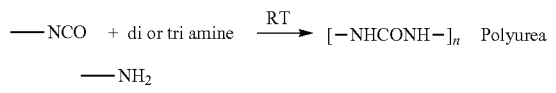
Polyurea (3)

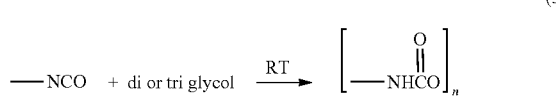
Polyurethane (4)

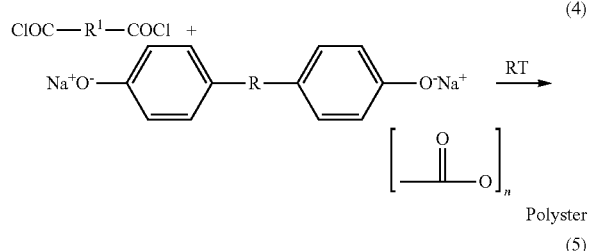
Polyester (5)

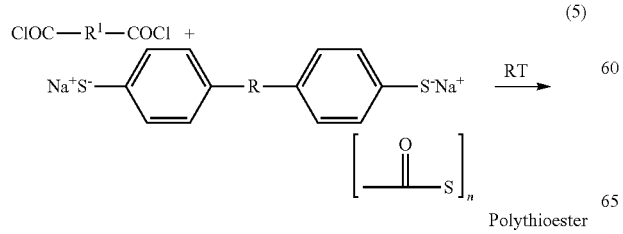
Polythioester

-continued (6)

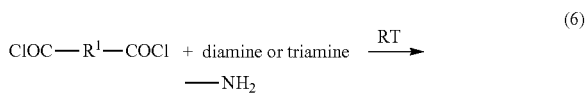
[—CONH—]$_n$ Polyamide (7)

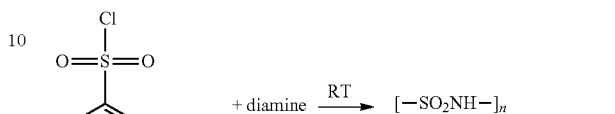
Polysulfonamide (8)

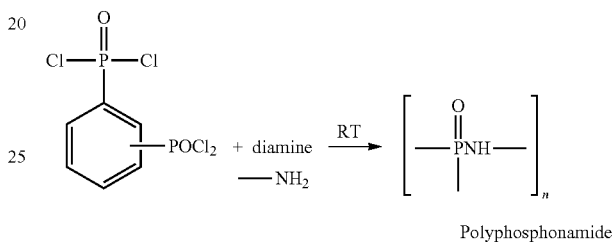
Polyphosphonamide (9)

ClOCO—R—OCOCl + —OH $\xrightarrow{RT}$ [—CO$_3$—]$_n$
Polycarbonate (10)

Cl—SiRR$^1$—Cl + H$_2$O $\xrightarrow{RT}$

[—SiRR$^1$—O—SiRR$^1$—]$_n$ Polysiloxane

For the purposes of the present invention however the polymer resin is preferably formed either by an in situ or two phase polymerisation reaction of an isocyanate moiety or alternatively by the condensation of an optionally etherified urea-formaldehyde prepolymer including both self-condensation or cross-linking with a suitable agent.

Thus according to a further aspect of the present invention there is provided a microcapsule having enhanced dispersibility comprising an encapsulated material enclosed within a solid permeable shell of a polymer resin having incorporated therein at least one surface modifying compound having one to eight functional moieties capable of reacting with at least one isocyanate group present on the wall forming material, which imparts surface activity when incorporated and wherein said surface modifying compound is selected from compounds having the formula

 (I)

 (II)

(III)

 (IV)

(V)

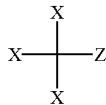

wherein Z is a moiety that contributes to modifying the surface properties of said microcapsule and each X is, independently, a functional moiety capable of reacting with isocyanate and the moieties designated by lines linking the X and Z functional groups have a molecular weight of between 50 and 4000, and may be optionally substituted aryl, hydrocarbyl, or heterocyclic units, or combinations thereof, optionally containing internally linked amino, ether, thioether, acetal, ester, thioester, amide, sulphonamide, urethane, urea, carbonate, siloxane, or phosphonamide groups or combinations thereof.

Thus in one aspect of the present invention the solid permeable shell of polymer resin is made by isocyanate polymerisation and the surface modifying compound reacts with the isocyanate moiety in the wall forming material. Such wall-forming processes involving either an in situ or two phase polymerisation reaction of an isocyanate moiety will be familiar to those skilled in the art and may be used in the process of the present invention. Suitable isocyanates include, inter alia, aromatic isocyanates such as isomers of tolylene diisocyanate, isomers and derivatives of phenylene diisocyanate, isomers and derivatives of biphenylene diisocyanates, polymethylenepolyphenyleneisocyanates (PMPPI), aliphatic acyclic isocyanates such as hexamethylene diisocyanate (HMDI), cyclic aliphatic isocyanates such as isophoronediisocyanate (IPDI) and trimers of HMDI. Mixtures of isocyanates may also be used.

Methods of varying the permeability and thickness of the wall are well known to those skilled in the art and include the type and amount of wall-forming material and the degree of cross-linking used. The present invention may be directed to microcapsule systems having a wall which presents either a significant or a more transient barrier to release of the core material. Thus for example microcapsules of the present invention will not generally release the core material until after application to the desired target or utility, although for some applications the microcapsule wall may be designed to be ruptured on or immediately after application. Alternatively the microcapsules of the present invention may be designed to release core material slowly over a period of time or may be sufficiently robust or to be dried and then re-dispersed. In general it is preferred that the weight ratio of the wall material to the microcapsule (core plus wall) is greater than 1% by weight. Typically the weight ratio will be from 1% to 70% or more specifically from 3% to 15%.

The chemistry of microcapsule wall formation from isocyanate molecules with a functionality of 2 or more typically involves reaction with a molecule having two or more functional groups capable of reaction with the isocyanate group. Established preparative methods for predominantly polyurea microcapsules typically involve reaction of the isocyanates with amino-groups.

Thus typical isocyanate wall-forming reactions include the reaction with an amine moiety to form a polyurea or with a di or tri glycol to form a polyurethane. The isocyanate molecules are usually contained within the oil phase in the above described processes. The amino groups may be either generated in situ in the oil phase at the oil-water interface as described for example in U.S. Pat. No. 4,285,720, incorporated herein by reference, or may be added through the aqueous phase as described for example in U.S. Pat. No. 4,280,833, incorporated herein by reference. Cross-linking may be accomplished by the inclusion of isocyanates having a functionality of greater than 2, or by adding amine compounds such as diethylenetriamine with a functionality of greater than 2.

More specifically as described in U.S. Pat. No. 4,285,720, a polyurea microcapsule involves the use of at least one polyisocyanate such as polymethylene polyphenyleneisocyanate (PMPPI) and/or tolylene diisocyanate (TDI) as the wall-forming material. In the in situ creation of such polyurea microcapsules, the wall-forming reaction is initiated by heating the emulsion to an elevated temperature at which point some isocyanate groups are hydrolyzed at the interface to form amines, which in turn react with unhydrolyzed isocyanate groups to form the polyurea microcapsule wall.

The present invention is also applicable to variations in conventional wall-forming processes. For example the incorporation of acetal containing structures to form acid-triggerable microcapsules is described in PCT Patent Application WO 00/05952.

Catalysts may be used to promote reaction between isocyanates and nucleophiles, particularly when the nucleophile or the isocyanate is relatively unreactive. When such reaction is accomplished in a homogeneous oil phase, catalysts such as dibutyltin dilaurate are suitable. When such reaction is accomplished at the interface of an oil-in-water emulsion, phase transfer catalysts such as those described in U.S. Pat. No. 4,140,516 are suitable.

Whilst the isocyanate-based process of the present invention is generally applicable to a wide range of isocyanate wall-forming reactions such as those described above, the in situ polyurea process such as that described in U.S. Pat. No. 4,285,720 and the two phase process such as that described for example in U.S. Pat. No 4,280,833 are generally most convenient.

According to a still further aspect of the present invention there is provided in a process for the production of microcapsules by self-condensation of an optionally etherified urea-formaldehyde prepolymer, wherein an emulsion is prepared in which the discontinuous phase contains the prepolymer and one or more materials to be encapsulated, and wherein microcapsules are formed by self-condensation of the prepolymer adjacent to the interface between the discontinuous phase and the continuous phase of the emulsion, the step comprising reacting the prepolymer, before and/or after preparation of the emulsion, with a surface-modifying agent selected from compounds having the formula

where X is OH, SH, or NHA, A is hydrogen or $C_1$-$C_4$ alkyl and Z is a moiety that contributes to modifying the surface properties of a microcapsule shell produced by self-condensation of the prepolymer, and the moieties designated by lines linking the X and Z functional groups have a molecular weight of between 50 and 4000, and may be optionally substituted aryl, hydrocarbyl, or heterocyclic units optionally containing internally linked amino, ether, thioether, acetal, ester, thioester, amide, sulphonamide, urethane, urea, carbonate, siloxane, or phosphonamide groups or a combination thereof.

In addition to self-condensation of the optionally etherified urea-formaldehyde prepolymer, the scope of the present invention also includes the optional inclusion of a crosslinking agent providing cross-linking condensation between the pre-polymer and the cross-linking agent.

Thus preferred materials utilized in forming the wall of the microcapsules of this invention also include optionally etherified urea-formaldehyde resins, (urea-fornaldehyde prepolymers). Preferably they are etherified and comprise urea-formaldehyde prepolymers or resins in which the methylol ($-CH_2OH$) groups have been etherified by reaction with an alcohol, preferably a $C_4$-$C_{10}$ alkanol, most preferably n-butanol. Preferably from about 50 to about 98%, and most preferably from about 70 to about 90% or from about 70 to about 95%, of the methylol groups in the prepolymer have been etherified.

Etherified urea-fornaldehyde prepolymers suitable for use in the invention include those available, for instance, under the Beetle trademark from American Cyanamid, the Resimene trademark from Solutia, and the Beckamine trademark from Reichold Chemicals.

Processes for production of aminoplast microcapsules in the present invention are described in U.S. Pat. Nos. 4,956,129 and 5,332,584, which are hereby incorporated herein by reference. In general, the chemistry is believed to involve the self-condensation of the etherified urea-formaldehyde prepolymer. Cross-linking and other wall-modifying agents such as pentaerythritol and pentaerythritol derivatives may be included in the process to provide additional cross-linking. Other suitable cross-linking agents include those containing hydroxyl, amine and thiol functional groups, particularly polythiols. One particularly useful cross-linking agent described in the above-mentioned U.S. patents is pentaerythritol tetrakis (3-mercaptopropionate), sold under the trademark Mercaptacetate Q-43 Ester.

The exact nature of the wall chemistry of these microcapsules is not known for certain, and we do not wish to be bound by theory. However, it is believed that self-condensation or cross-linking of methylol and/or etherified methylol groups in the prepolymer involves the formation of new ether and/or thioether and/or $-NCH_2N-$ groups.

It will be appreciated that the chemistry of the reaction of the group $-X$ with the wall-forming material will vary as between the various isocyanate systems and aminoplast systems and different surface-modifying agents may be preferred depending on the wall-forming system used. Isocyanate systems will be considered first.

The surface modifying compounds of the present invention contain one or more functional groups (designated as X) capable of reacting with wall forming material, in this instance with isocyanate. The reactions of the moiety X with isocyanates are illustrated herein below using structure (IA) for simplicity although the reactions of the remaining structures correspond accordingly. For example, carboxylic acids react with isocyanates to form mixed anhydrides that rapidly eliminate carbon dioxide with the formation of carboxylic amides:

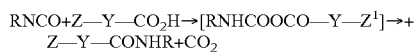

Thiol, hydroxyl and amino groups react with isocyanates to form respectively thiocarbamate, urethane, and urea linkages:

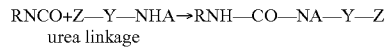

While any functional group of the above types may be used to introduce surface modifying compounds into the microcapsule walls of the present invention, hydroxyl and amino groups are particularly preferred unless a slower reaction is desired as discussed below. The preferred groups are chosen on the basis of the process and on the desired properties of the microcapsule wall as is discussed in greater detail below.

The reactivity of the functional group with the isocyanate influences the process of choice. For example, the reaction with amines is very fast, allowing modification from an agent in the aqueous phase with wall-forming materials in the oil phase. In contrast, the reaction with alcohols or thiols is much slower and may compete less favourably with hydrolysis of the isocyanate if the surface modifying compound is introduced from the aqueous phase. Reaction of isocyanates with these molecules is thus more readily accomplished in the oil phase.

The stoichiometry of the reaction of the surface-modified compound and the isocyanate will determine the degree of polymerization of the resulting surface modifying compound to be incorporated into the wall. For example, with only a slight excess of the total isocyanate moieties over the total $-X$ moieties for difunctional (i.e. with two groups X) surface modifying compounds and difunctional isocyanates, relatively high molecular weight material may be produced. In certain instances, this product may be soluble in the aqueous phase and therefore may not be readily available for incorporation into the wall. Such a case may arise, for example, with a diol surface modifying compound or prepolymer carrying several sulphonate groups. At higher ratios of isocyanate to surface modifying compound, lower degrees of polymerization result.

It will be appreciated however that in any event the polymer initiating groups of the wall-forming material, for example the isocyanate groups, should not be fully reacted with surface modifying compound since wall-formation cannot then take place. Whilst in some situations wall formation may take place in competition with the reaction between isocyanate and the surface modifying compound even at stoichiometries of about 1:1, it is preferred that there is an excess of (total) isocyanate groups over (total) groups $-X$.

Thus for example in the reaction between a difunctional isocyanate wall-forming material such as TDI and a difunctional surface modifying compound (i.e. a surface modifying compound having two groups $-X$) such as dimethylolpropionic acid (DMPA) molar ratios of TDI:DMPA of from 4:1 to 15:1 are preferred.

When the surface modifying compound is added via the aqueous phase, the degree of modification may be altered by changing the mass in the aqueous phase whilst keeping the amount of isocyanate the same.

Typically, the surface modifying compounds of the present invention have molecule weights of about 2000 or less. It may be preferred to have molecular weights of less than 10,000 in prepolymers that have been reacted with the surface modifying compound(s).

Thus in general the preferred ratio of the total moiety(ies) —NCO in the wall-forming material to the total reactive moiety(ies) —X in the surface modifying compound is from 2:1 to 25:1 and more preferably from 4:1 to 15:1. Thus for example when a difunctional isocyanate (such as TDI) is reacted with a difunctional surface modifying compound (such as DMPA) this ratio remains 2:1 to 25:1 and more preferably from 4:1 to 15:1 on a molar basis, whilst for PMPPI (a multifunctional typically isocyanate with an average functionality of 2.7) reacted with a monofunctional surface modifying compound such as MeOPEG, this equates to molar ratios of PMPPI:MeOPEG of from 0.75:1 to 9.3:1 and more preferably from 1.5:1 to 5.6:1.

Where more than two functional groups (X) are present in either the surface modifying compounds or the isocyanates, it is possible to generate cross-linking reactions. These reactions may be undesirable if they occur before the wall-formation proper takes place. When two functional groups are present in the surface modifying compound, reaction with a difunctional isocyanate will result in a linear chain-extended surface modified molecule. The use of excess difunctional isocyanate in the reaction controls the degree of polymerization of the isocyanate extended product. It may be preferred to have alpha-omega isocyanate terminated molecules. In order to minimize or avoid cross-linking until the desired moment, isocyanates having a functionality of greater than 2 are preferably added to the oil after the chain extension reaction and before emulsification.

When one functional group (—X) is present in the surface modifying compound, it may be preferred to react this molecule with an isocyanate having a functionality of greater than or equal to two. Thus for example MeOPEG may suitably be reacted with PMPPI. The unreacted isocyanate groups can then be used to polymerize by chain extension with other wall-forming materials. Surface modifying compounds having two or more functional groups (—X) may be used if the level of cross-linking with isocyanates prior to wall formation takes place can be controlled. This may be achieved, for example, by reacting surface modifying compounds having a functionality of only slightly greater than 2 with an excess of difunctional isocyanate prior to the optional addition of isocyanates having a functionality greater than 2 to the oil phase after the chain extension reaction and before emulsification. Such a situation, employing the sulphonate polyester polyol illustrated by structure (V) is described in Example 6 below. Alternatively, surface modifying compounds with a functionality greater than 2 may be mixed with isocyanates having a functionality greater than or equal to 2, provided that the reaction between the surface modifying compound and isocyanate molecules can be inhibited until the oil has been emulsified in water.

In terms of the aminoplast system, the surface-modifying agents of the present invention contain one or more functional groups (designated as —X) capable of reacting with methylol and etherified methylol groups. Their reactions with the wall-forming urea formaldehyde prepolymers are illustrated herein below using structure (IA) for simplicity although the reactions of the remaining structures correspond accordingly.

For example, hydroxyl groups of a surface-modifying agent are believed to react with methylol or ether groups in the prepolymer to form ether linkages:

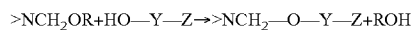

where R is hydrogen (forming a methylol group) or $(C_4-C_{10})$ alkyl (forming an ether group). Note, however, that under certain conditions this reaction may be reversible and the product containing a new ether linkage >NCH$_2$—O—Y—Z may not be sufficiently stable under the process conditions.

Amino groups in a surface-modifying agent are believed to react with methylol or ether groups in the prepolymer to form amino linkages:

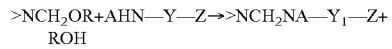

where A is hydrogen or $C_1$-$C_4$ alkyl. This reaction is expected to be less reversible than the above ether-producing reaction, and the products more stable.

Thiol groups in a surface-modifying agent are believed to react with the methylol or ether groups in the prepolymer to form thioether linkages:

>NCH$_2$OR+HS—Y—Z→>NCH$_2$'S—Y—Z+ROH

This reaction is expected to be less reversible than the above ether producing reaction and the products more stable. In general therefore it is preferred that —X is an amino or in particular a thiol group when an aminoplast system is used.

The reactivity of the functional group in the surface-modifying agent with the prepolymer influences the choice of process as well as of the surface-modifying compound. For example, the reaction with thiols is less reversible than that with alcohols, allowing modification from a surface modifying compound in the aqueous phase with wall-forming materials in the oil phase.

The stoichiometry of the reaction of the surface modifying compound with the alkylated urea-formaldehyde pre-polymer will depend on: (i) the structure and molecular weight of both the modifier and the resin, (ii) the required degree of modification, (iii) the mechanism of the reaction.

Commercial alkylated U—F resins are available in a range of molecular weights and degrees of alkylation. For the purpose of illustration only a simplified representation of a repeat unit in the resins used in this invention is given by the formula —[N(CH$_2$OR)—CO—N(CH$_2$OR)—CH$_2$]$_n$— where R is hydrogen (forming a methylol group) or $C_4H_9$— (forming a butyl ether group) and n has a value between 1 and 1000.

The surface modifying compounds are reacted with the —OR groups as described above in a ratio which is preferably determined by routine experimentation and where sufficient of the OR groups are reacted so as to impart surface-active properties to the modified resin, with sufficient OR groups remaining to enable self-condensation or cross-linking reactions to form the microcapsule wall. If an excess of OR groups are reacted the modified resin may become water soluble and thus unavailable for incorporation into the capsule wall. For a given molecular weight, the greater the hydrophilicity of the surface modifying agent the lower will be the stoichiometric ratio of agent:OR groups necessary to impart surface-active properties. For example, and in general for a given molecular weight a lower stoichiometric ratio of agent:OR groups would be required for sulphonate containing than carboxylate containing surface modifying agents. For a given structural type of surface modifying agent such as a methoxy-polyethylene glycol MeO(EO)$_m$— the higher the molecular weight (value of m) the lower will be be the ratio of agent:OR groups necessary to impart surface-active properties. In addition, the preferred stoichiometric ratio of agent:OR groups may depend on the relative reactivity of the surface-modifying agent with methylol and with butyl ether groups on the resin.

It has been found convenient to estimate the amount of surface modifying compound used based roughly on the number of theoretical U—F repeat units (where the degree of alkylation is as defined by the supplier of the resin) in a given molecular weight of the alkylated U—F resin. Preferred stoichiometric mole ratios surface modifying agent:U—F repeat unit are between 1:40 to 1:4.

The choice of the preferred surface modifying compound for use with any given microcapsule wall-forming system will depend on a range of factors. Thus for example in the isocyanate polyurea system there are practical advantages in addition of the surface modifying compound through the aqueous phase, for which process it is preferred that —X is amino. On the other hand there are other advantages in the pre-reaction of isocyanate with the surface modifying compound, and in particular it is an advantage that the course of reaction can be monitored using infra-red analysis. When —X is thiol or hydroxy it is preferred that's the reaction with isocyanate takes place before emulsification. Clearly however the ease and convenience of the reaction of the surface modifying compound with the isocyanate group(s) is not the only factor to be considered. Once reaction has taken place the nature of the surface modification provided by the remainder of the surface modifying compound becomes key. In commercial terms the cost of the surface modifying compound is also a factor to be considered.

The nature of the core material is not critical to the scope of the present invention and any material suitable for microencapsulation may be used as core material. The benefits of the present invention may however be of particular relevance to specific core materials and applications. For example the microcapsules of the present invention will find particular utility in applications for which microcapsule stability, aggregation and re-dispersibility tend to present problems. The core material is typically a liquid and, in the case of agricultural products, may be comprised of one or more pesticides, or, in the case of non-agricultural products, may be comprised of inks, dyes, biological actives, pharmaceuticals or other products. For agricultural products, the core may be an organic solution, typically immiscible with water, comprising one or more pesticides as the active ingredient, including insecticides, herbicides, fungicides and biocides. The pesticide may be a liquid, a solid pesticide that has been dissolved in a solvent that is immiscible with water, or a solid suspended in the organic solution that may have within it another pesticide. The organic solution may also have an photostabilising protectant suspended or dissolved within it.

Any agrochemical which is suitable for microencapsulation may be used, but by way of illustration only, examples of suitable herbicides are s-triazines, e.g., atrazine, simazine, propazine, cyprozine; Sulphonylureas e.g., chlorsulfuron, chlorimuronethyl, metsulfuronmethyl, thiameturon-methyl; foramsulfuron, iodosulfom and Triketones e.g., sulcotrione. Another suitable compound is the fungicide (E)methyl-2-[2-(6-(2-cyanophenoxy)pyrimidin-4-yloxy)phenyl]-3-methoxypropenoate.

Examples of suitable insecticides include permethrin, cypermethrin, deltamethrin, fenvalerate, cyfluthrin, resmethrin, allethrin, etofenprox tefluthrin and lambda-cyhalothrin.

The liquid in which the solid is suspended may suitably be a second herbicide, especially a thiocarbamate or a haloacetanilide, and preferably acetochlor. The haloacetanilides, particularly the subclass generally known as α-chloroacetanilides, are a well-known class of herbicidal agents and have been used and proposed for use in a number of crop and non-crop applications. Some of the better known members of this class include α-chloro-6'-ethyl-N-(2-methoxy-1-methyl-ethyl)-acetanilide (metolachlor), N-butoxymethyl-α-chloro-2',6'-diethylacetanilide (butachlor), α-chloro-2',6'-diethyl-N-methoxymethylacetanilide (alachlor), 2-chloro-N-(ethoxymethyl)-6'-ethyl-o-acetotoluidide (acetochlor) and α-chloro-N-isopropylacetanilide (propachlor). Many other compounds of this type are disclosed in numerous patents.

The thiocarbamates are a well known class of herbicide which includes Molinate (S-ethyl hexahydro-1H-azepine-1-carbothioate); Butylate (S-ethyl diisobutylthiocarbamate); EPTC (ethyl dipropylthiolcarbamate); Triallate (2,3,3-trichloroallyl-diisopropylthiolcarbamate); Diallate (cis-1-trans-2,3-dichloroallyl-diisopropylthiolcarbamate); and Vernolate (S-propyl dipropylthiolcarbamate). When the liquid is an herbicide, the microcapsules of the invention suitably contain 0.1-55% by weight of biologically active compounds.

The liquid may alternatively be any organic solvent that is immiscible with water, and is polar enough to dissolve the monomers, oligomers or prepolymers used to form the walls of the microcapsules Suitable solvents are well known to those skilled in the art. By way of illustration, examples of such solvents are aromatic compounds such as xylenes or naphthalenes, especially Solvesso 200; aliphatic compounds such as aliphatic or cycloaliphatic hydrocarbons, for example hexane, heptane and cyclohexane; alkyl esters such as alkyl acetates for example Exxate 700 or Exxate 1000 and such as alkyl phthalates for example diethyl phthalate and dibutylphthalate; ketones such as cyclohexanone or acetophenone; chlorinated hydrocarbons; and vegetable oils. The solvent may be a mixture of two or more of the above solvents. A safener for either herbicide may be present, and many such safeners or antidotes are well known in the art. Preferred types for use with haloacetanilide herbicides include dichloroacetamides such as dichlormid (N,N-diallyl dichloroacetamide); 2,2,5-trimethyl-3-dichloroacetyl oxazolidine (R-29148),N-dichloroacetyl-1-oxa-4-azaspiro[4,5]decane (AD-67); 4-dichloroacetyl-2,3-dihydro-3-methyl-1,4-benzoxazine (CGA-154281); 1-(dichloroacetyl)hexahydro-3,3, 8a-trimethylpyrrolo-[1,2-a]-pyrimidin-6(2H)-one and N-(1, 3-dioxolan-2-yl-methyl)-N-(2-propenyl)-2,2-dichloroacetamide (PPG-1292). These and other dichloroacetamides are described, for instance, in U.S. Pat. Nos. 4,124,372; 4,256,481; 4,294,764; 4,448,960; 4,601,745; 4,618,361; 4,708,735 and 4,900,350. Additional known types of safeners or antidotes include certain oxime derivatives (U.S. Pat. Nos. 4,070,389 and 4,269,775, for instance), thiazole carboxylic acids and derivatives (U.S. Pat. No. 4,199,506 for instance), haloacyltetrahydroisoquinolines (U.S. Pat. No. 4,755,218, for example), aryl cyclopropane carbonitriles (U.S. Pat. No. 4,859,232, for example) and 1,8-naphthalic acid, its anhydride and derivatives. Safeners or antidotes, when included, will usually be contained in the organic or water-immiscible phase.

When a photostabilising protectant is used in this invention, it is preferably titanium dioxide, zinc oxide, or a mixture of titanium dioxide and zinc oxide. In general, the photostabilising protectant is used in an amount of from about 0.1 to about 50 weight %, preferably from about 1 to about 10 weight %, with respect to the organic phase. Mixtures of titanium dioxide and zinc oxide will contain these two substances in a weight ratio of from about 1:10 to about 10:1.

Biologically active materials suitable for the present invention that are subject to degradation or decomposition by ultraviolet light and therefore requiring a protectant include the pyrethroids and pyrethrins. Many of the pyrethroids known to be susceptible to degradation by ultraviolet light include permethrin, cypermethrin, deltamethrin, fenvalerate, cyfluthrin, resmethrin, allethrin, etofenprox, and lambda-cyhalothrin. Other biologically active materials that are known to be susceptible to degradation or decomposition by ultraviolet light include the herbicides trifluralin, ioxynil and napropamide, the insecticides pirimiphos-methyl and chlorpyrifos and the fungicide azoxystrobin. Microcapsules of this invention may contain two or more ultraviolet light sensitive biologically active materials.

The liquid utilized in this invention may be a liquid biologically active material which itself is susceptible to degradation by ultraviolet light, or a biologically active material which is not normally so susceptible (but in which there is suspended a second biologically active material which is light-sensitive), or an organic solvent which is immiscible in water and in which the ultraviolet light sensitive material is suspended or dissolved. The liquid, in any case, should be sufficiently polar to dissolve the prepolymer or prepolymers used to form the microcapsule wall.

Capsule suspensions of the present invention may also be produced containing two materials that may be incompatible with each other, with one material encapsulated and the other contained in the aqueous phase of the suspension. Such combination products are storage stable and enable, for example, the production of a combination pesticidal product wherein incompatible pesticides may be applied together.

Those skilled in the art will be readily able to apply conventional processes for the preparation of microcapsules according to the invention in non-agrochemical fields including but not limited to encapsulated dyes, inks, pharmaceuticals, flavouring agents and fragrances. Oil-in-water techniques are generally more suitable although the present invention also includes water-in-oil microencapsulation techniques. Conventional solvents may be used for the oil phase such as those described above in connection with microcapsules for agrochemical use.

According to a further aspect of the present invention there is provided a modified process for the encapsulation of a dispersed material within a solid permeable shell of a polymer resin formed by polymerisation of a wall-forming material which comprises incorporating a surface modifying compound having a formula (I), (II), (III), (IV) or (V) as hereinbefore defined into the polymer resin.

The incorporation of the surface modifying compound in the polymer resin wall of the microcapsule may take place at various stages during the microencapsulation process.

Process 1

One process for preparing such microcapsules comprises pre-reacting the surface modifying compound and a wall-forming material (for example a monomer, oligomer or prepolymer) in an organic phase, for example:
(a) reacting a surface-modifying compound or agent with at least one wall-forming material thereby forming a modified surface-active intermediate;
(b) preparing an organic solution or oil phase comprising the material to be encapsulated, the modified surface-active intermediate, and, optionally, additional wall-forming material;
(c) creating an emulsion of the organic solution in a continuous phase aqueous solution comprising water and, optionally, a protective colloid, wherein the emulsion comprises discrete droplets of the organic solution dispersed throughout the continuous phase aqueous solution, with an interface formed between the discrete droplets of organic solution and the aqueous solution; and either
(d) causing in situ polymerization and/or curing of the modified wall-forming material in the organic solution of the discrete droplets at the interface with the aqueous solution by heating the emulsion for a sufficient period of time andoptionally adjusting the pH to a suitable value to allow substantial completion of wall formation, thereby converting the organic solution droplets to capsules consisting of solid, permeable, modified polymer shells enclosing the material, or as an alternative to (d)
(e) causing polymerization at the oil-water interface by bringing together a wall forming material added through the aqueous continuous phase and capable of reacting with the wall forming material(s) in the discontinuous oil phase.

In stage (a) above the pre-reaction of the surface modifying compound and the wall-forming material to form the surface-active intermediate may either take place in the organic phase to be encapsulated or in a different or separate organic phase from which the modified surface-active intermediate may optionally be isolated before use in stage (b).

In stage (d) above and in corresponding stages of the processes described below, aminoplast systems generally required adjustment of the pH. Adjustment of the pH is sometimes also used in isocyanate systems.

Process 1 above is suitable for both aminoplast and isocyanate wall-forming systems. The functionality of the wall-forming material and the surface modifying compound respectively should preferably be such that their reaction does not lead to excessive cross-linking such that the emulsification or subsequent wall-forming reactions are adversely affected. Thus for example for reaction with difunctional isocyanates mono- or difunctional surface modifying compounds are preferred. For reaction with isocyanates having a functionality greater than 2, monofunctional surface modifying compounds are preferred. For reaction with polyfunctional alkylated urea-formaldehyde resins monofunctional surface modifying compounds are also preferred.

Certain intermediates produced by reaction of the wall-forming material and the surface-modifying compound in step (a) are novel, as is the process for their preparation, and both the intermediates and processes for their preparation constitute further aspects of this invention Process 2

A second process for preparing such wall-modified microcapsules comprises preparing an organic solution or oil phase comprising the material to be encapsulated, the surface modifying compound and the wall-forming material, and allowing the surface modifying compound to react with the wall-forming material under the conditions of the in situ polymerization and/or curing, for example;
a) preparing an organic solution or oil phase comprising the material to be encapsulated, the surface modifying compound and the wall-forming material
b) creating an emulsion of the organic solution in a continuous phase aqueous solution comprising water and, optionally, a protective colloid, wherein the emulsion comprises discrete droplets of the organic solution dispersed throughout the continuous phase aqueous solution, with an interface formed between the discrete droplets of organic solution and the aqueous solution; and either
c) causing in situ polymerization and/or curing of the modified wall-forming material in the organic solution of the discrete droplets at the interface with the aqueous solution by heating the emulsion for a sufficient period of time and optionally adjusting the pH to a suitable value to allow substantial completion of wall formation, thereby converting the organic solution droplets to capsules consisting of solid, permeable, modified polymer shells enclosing the material; or optionally in addition to (c)
d) causing polymerization at the oil-water interface by bringing together a wall forming material added through the aqueous continuous phase and capable of reacting with the wall forming material(s) in the discontinuous oil phase.

Process (2) above is suitable for both the isocyanate and aminoplast wall-forming systems. The functionality of the wall-forming material and the surface modifying compound is not critical. Preferably the reactivity of the group(s) —X with the wall-forming material are such that incorporation of the surface modifying compound into the wall material takes place at the oil-water interface before or at the same time as wall formation and the reaction product of the surface modifying compound and the wall-forming material remains at the interface rather than dissolving in the aqueous phase.

Process 3

In a third process, the surface modifying compound may be incorporated in the aqueous phase rather than the organic phase. Thus a third process for preparing wall-modified microcapsules comprises:
  (a) preparing an organic solution or oil phase comprising the material to be encapsulated and the wall-forming material;
  (b) creating an emulsion of the organic solution in a continuous phase aqueous solution comprising water and the surface-modifying compound(s), wherein the emulsion comprises discrete droplets of the organic solution dispersed throughout the continuous phase aqueous solution, with an interface formed between the discrete droplets of organic solution and the aqueous solution; and
  (c) causing in situ polymerization and/or curing of the wall-forming material so that the surface-modifying molecule(s) is incorporated into the wall by heating the emulsion for a sufficient period of time and optionally adjusting the pH to a suitable value, to allow substantial completion of wall formation, thereby converting the organic solution droplets to capsules consisting of solid, permeable, modified polymer shells enclosing the material.

Process (3) above is suitable for both the isocyanate and aminoplast systems. Process (3) is especially preferred for the polyurea system when the surface modifying compound contains amino group(s) —X in that amino groups react with isocyanate groups relatively faster than do hydroxyl or thiol groups.

Process 4

In an alternative to Process (3) described above, the surface modifying compound is incorporated into the aqueous phase and is incorporated into the wall-forming material at the oil-water interface. Wall-formation is achieved in a two phase system by the subsequent addition of wall-forming material through the aqueous phase. Thus a fourth process for preparing wall-modified microcapsules comprises:
  (a) preparing an organic solution or oil phase comprising the material to be encapsulated and a first wall-forming material(s);
  (b) creating an emulsion of the organic solution in a continuous phase aqueous solution comprising water and the surface-modifying compound(s), wherein the emulsion comprises discrete droplets of the organic solution dispersed throughout the continuous phase aqueous solution, with an interface formed between the discrete droplets of organic solution and the aqueous solution whereupon the surface modifying compounds(s) react at the interface with wall forming material from the organic phase; and
  (c) causing polymerization at the oil-water interface by bringing together a second wall forming material added through the aqueous continuous phase and capable of reacting with the first wall forming material(s) in the discontinuous oil phase.

Process (4) is particularly suitable for the polyurea wall-forming system. Preferred surface modifying compounds for use in Process (4) contain group(s) —X which are amino groups that are capable of reacting rapidly with isocyanates at the aqueous/oil interface. Preferred second wall-forming materials added through the aqueous phase also contain amino groups for the same reason.

It will be appreciated that in certain instances the above processes may be combined to incorporate two or more surface modifying compounds. Thus for example a first surface modifying compound may be pre-reacted with the wall-forming material in accordance with Process 1 whilst a second surface modifying compound may be added through the aqueous phase in accordance with Process (3).

For each of the above in situ processes, the reverse may be done, i.e., encapsulation of a water-soluble substance in a continuous oil phase. In this process of the invention the wall-forming material or prepolymer must be soluble in water. Thus for example in the urea-formaldehye system it is desirable to use a urea-formaldehyde prepolymer that has not been etherified, i.e. has free methylol groups.

Whether the process employs an oil/water emulsion or a water/oil emulsion, surface-modifying agents may be introduced into either the oil or the water phase, or both. However, surface-modifying agents that are introduced into the phase containing the wall-forming material must desirably be of such nature, or be introduced in such a manner, that they do not react with the wall-forming material so as to cause premature and undesired cross-linking prior to the wall formation or polymerization step (otherwise proper wall formation would be impeded or impossible at that stage).

Microcapsules having surface modifying compounds built into their walls and formed by processes such as those illustrated above are capable of exhibiting various properties in addition to varying their release characteristics in respect of the core material by altering the permeability of the wall-material. These include, for example, improved stability of the capsules, improved dispersability, prevention of agglomeration of the capsules (wherein the surface modification acts as a protective colloid), reduction or elimination of particle size growth, improved thermal storage stability, and improved formulation compatibility. Because these compounds are incorporated into the microcapsule wall structure they are not so readily desorbed as may occur with conventional physically adsorbed surfactants. Moreover by virtue of surface modification and size, certain of the micro- and nano-capsules of the present invention show greater mobility in soil than do similar capsules no so modified. By having either reduced levels of or no free surfactant, in contrast to present microcapsule suspensions, foaming is reduced or eliminated. The redispersability of these wall-modified microcapsules from the dry state is enhanced. Also, the size of the microcapsule can be better controlled. Particle size in traditional microcapsules is controlled by shear and amount of emulsifier used to make the emulsion. High levels of surfactants, which normally work by adsorption at the interface, can often adversely affect the integrity of the microcapsule wall. The present invention resides in both the process for preparing such microcapsules and the microcapsules thus formed.

One aspect of this invention describes microcapsule wall compositions having one or more surface modifying compounds bonded therein. These compounds may be anionic, cationic, zwiterionic, and/or nonionic in nature or various combinations of the same depending on the nature of the group Z. Charged agents may or may not be switchable between ionized and non-ionized forms. The presence of ionic groups at the surface of microcapsules provides a means of charge repulsion between adjacent particles and this aids colloid stability of the formulation. Charge repulsion may be between either separately positive or negative groups. Examples of positively charged groups —Z include quaternary ammonium. Examples of negatively charged groups —Z include sulphonate, carboxyl and phosphonate. Colloid stabilization may alternatively be effected by non-charged hydrophilic moieties that maintain stability by preventing particles from interacting by steric repulsion. Examples of such moieties include oxyethylene—containing polymers. The surface-modifying compounds may further serve to change the properties of the microcapsule wall such that the capsules may, for example, become more or less adhesive to a particular surface The preferred method of stabilization will depend upon the desired application of the microcapsule product. For example, positively charged structures may adhere strongly to negatively charged biological material such as foliage and soil.

The invention is further illustrated by the following examples; however such examples should not be interpreted as a limitation on the invention:

Exemplification of Capsule Formation

Example 1

Incorporation of an anionic sulfonate diol into the polyurea walls of microcapsules containing Acetochlor using Process (1) above.

This experiment demonstrated that a sulfonate diol can be incorporated into microcapsule walls by attachment to tolylene diisocyante ("TDI") in the oil phase prior to encapsulation.

A sulfonate diol of the following formula

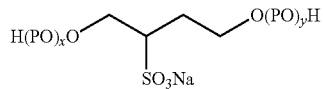

where x+y=3, 4 or 6, was reacted with tolylene diisocyanate ("TDI") forming a chain-extended surface modifying compound according to the following reaction The sulfonate diol was dissolved in methylene chloride ($CH_2Cl_2$) and gradually added at room temperature to a methylene chloride solution of TDI while stirring. The mixture was heated to 35° C. and analyzed by an IR spectrometer to monitor the progress of the reaction which was indicated by the diminishing of the —OH stretching peak at $3400\,cm^{-1}$ and the increasing of the polyurethane (—O—CO—NH—) peaks at $1720\,cm^{-1}$ (C=O) and $3300\,cm^{-1}$ (—NH—). After reaction, the methylene chloride was removed by increasing the temperature of the solution to 40° C. In order to minimize possible polymerization reactions, excess amounts of TDI were used in the reaction. The molar ratios of the sulfonate diol/TDI used were 1:3 and 1:5 (the stoichiometric ratio is 1:2).

The chain-extended TDI sulfonate diol (1.35 g) was added to an organic phase comprising a solution of the pesticide acetochlor (23.65 g), (dichlormid (N,N-diallyl-2,2-dichloroacetamide)) (3.93 g), polymethylene polyphenylene isocyanate ("PMPPI") (1.52 g), and Atlox 3409/Atlox 3404 emulsifier (0.95 g). This organic phase was then added to a separate aqueous phase comprised of water and either 0%, 1% or 2% REAX 100 M (a lignosulfonate available from Westvaco) as a protective colloid, and stirred at a fixed speed and time for each level of REAX 100M, thereby creating an oil-in-water emulsion. The emulsion was heated causing polymerization of the wall-forming material with sulfonate groups attached therein, thereby forming microcapsules averaging from 4.5 to 32 microns in diameter, depending upon the amount of protective colloid found within the aqueous phase.

Microcapsules formed with the sulfonate group derived from reaction of the surface modifying compound and the wall-forming material were compared against microcapsules prepared following the same process, but without the incorporation of the surface modifying compound. The compositions (1a and 1c below) containing surface modifying compounds had a greater emulsification effect than the compositions (1b and 1d below) without the surface modifying compounds, and required less energy for emulsification whilst producing smaller emulsion particles, and consequentially, smaller microcapsules as shown below

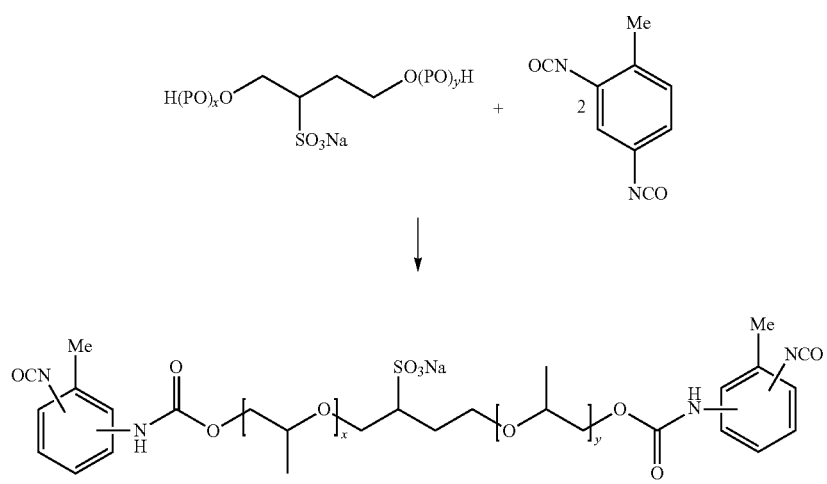

| Composition | Presence of Sulfonate Wall-Modifying Compound | % Protective Colloid in Aqueous Phase | Agitation | Emulsion Particle Size (microns) | State of Microcapsule Dispersion |
|---|---|---|---|---|---|
| 1a | Yes | 2% | 3000 rpm, 0.5 min | 4.5 | Fully dispersed |
| 1b | No | 2% | 3000 rpm, 1.0 min | 32 | Fully dispersed |
| 1c | Yes | 1% | 3000 rpm, 3.0 min | 10 | Fully dispersed |
| 1d | No | 1% | 3000 rpm, 3.0 min | 28 | Fully dispersed |
| 1e | Yes | 0% | 3000 rpm, 3.0 min | 25 | Fully dispersed |
| 1f | No | 0% | 3000 rpm, 3.0 min | 25 | Agglomerated and Gelled |

A dispersant, such as lignosulfonate or polyvinyl alcohol, is generally required in the microencapsulation process to stabilize the particles. In the presence of the sulfonate-containing wall modifying compound, a microcapsule formulation can be made without using any protective colloid, reflecting the dispersant function of the sulfonate moiety, as illustrated in the example above (Composition 1e). In contrast, formulations made in the absence of a protective colloid, i.e., without the incorporated surface modifying compound, gelled during reaction (1f). These results reflect the dispersant function of the sulfonate moiety due to the charges built into the wall through surface modification according to the invention. In the example the release rate of Acetochlor and dichlormid (N,N-diallyl-2,2-dichloroacetamide) was not affected by the incorporation of the surface modifying compound.

Example 2

Incorporation of an anionic sulfonate diamine (Poly-EPS 520-Na) into the polyurea walls of microcapsules containing Acetochlor using Process (3) above.

This experiment demonstrated that an anionic sulfonate diamine can be incorporated into microcapsule walls via reaction from the aqueous phase, thereby improving dispersibility and redispersibility of the capsules as well as affecting the release characteristics of the capsules.

A sulfonate diamine of the following formula $$H_2N\text{-}\!\!\!\!\!\!\!\overset{|}{\phantom{C}}\!\!\!\!\!\!\!\text{-}O\text{-}\!\!\left[\!\!\overset{|}{\phantom{C}}\!\!\!\!\!\!\!\text{-}O\right]_n\!\!\overset{|}{\phantom{C}}\!\!\!\!\!\!\!\text{-}\overset{H}{N}\text{-}\!\!\!\!\!\!\!\!\!\text{-}SO_3Na$$

commercially available from Raschig as Poly-EPS 520-Na, was used to prepare acetochlor-containing microcapsules. However, instead of pre-reacting the sulfonate diamine with TDI and then adding to the organic phase, the diamine was dissolved in the aqueous phase. Microcapsule formulations were then prepared as in Example 1 above with and without Reax 100M (protective colloid) in the aqueous phase of the formulation. The reaction between —NH₂ and/or —NH— and —OCN at the oil/water interface allowed the compound containing the sulfonate groups to chemically bond to the microcapsule wall.

The sulfonate diamine wall-modified microcapsules showed significant dispersant function. In the presence of the sulfonate diamine in the aqueous phase, well-dispersed strong microcapsules were formed without the use of the protective colloid Reax 100M. In contrast, in the absence of the protective colloid Reax 100M and the sulfonate diamine surface modifying compound, oil particles were recombined during the reaction and a glue-like gel was formed.

With respect to the release rate of Acetochlor from the microcapsules, small amounts of sulfonate diamine in the aqueous phase that were chemically bonded to the wall, e.g., 3.0% sulfonate diamine, reduced the release rate of the microcapsules. In contrast, larger amounts of sulfonate diamines, e.g., 6.0%, increased the release rate of Acetochlor.

Example 3

Incorporation of an anionic sulfonate diamine (Poly-EPS-520-Na) into the polyurea walls of microcapsules containing Lambda-cyhalothrin using Process 3 above. The use of certain water soluble polymers which coat microcapsules during spray drying and which aid redispersion is known in the art and is exemplified in EP 0869712 which is incorporated herein by reference. This experiment demonstrated that an anionic sulfonate diamine can be incorporated into microcapsule walls via reaction from the aqueous phase, markedly improving redispersibility of spray-dried capsules without the need for a polymeric coating, as well as improving the storage stability of those capsules.

Wall-modified microcapsule suspensions containing Lambda-cyhalothrin were prepared as described in Example 2 above. The lambda-cyhalothrin microcapsules produced had a typical wall of approximately 7.5 weight percent of the microcapsule. The capsule suspensions were diluted in equal ratios with water and then spray-dried using a Buchi Mini Spray Drier unit. The spray-drying conditions were as follows:

| | |
|---|---|
| Air Spray Rate | 600 |
| Inlet Temperature | 140° C. |
| Outlet Temperature | 70° C. |
| Feed Rate | Adjusted between 3 and 5 ml/min in order to maintain outlet temp |

The ability of the dry powder to spontaneously redisperse when added to water was assessed. The particle distribution and size was evaluated by adding the dry product to water in a vial that was inverted 10 times. The resulting dispersion was then screened by optical microscope and an LS-Coulter particle size analyzer. The test was carried out at initial day and after storage of the dry product in a sealed container at 50° C. for three days, 10 days and three weeks respectively. The results of the surface modified capsules versus non-surface modified capsules are given in the Table below:

| | Additives (Based on Dry Product) | | | Redispersion Test - Average Particle Size Distribution* | | | |
|---|---|---|---|---|---|---|---|
| | | | | | | 10 | 3 |
| | | | | Initial | 3 Days | Days at | Weeks |
| Polymer | Dispersant | Wetter | Salt | Day | at 50° C. | 50° C. | at 50° C. |
| Non-Surface Modified Capsules | None | 15% Lomar D | 1.5% Gerapon T-77 | 10% $CaCl_2$ | 37.3 microns | 63.3 microns | 64.5 microns | 40.2 microns |
| Surface Modified Capsules | None | 15% Lomar D | 1.5% Gerapon T-77 | 10% $CaCl_2$ | 4.0 microns | 5.1 microns | 9.0 microns | 8.8 microns |

*mean microcapsule diameter was approximately 2.5 microns.

The above results shows that wall modified microcapsules significantly improve redispersibility of spray dried capsules versus non-modified capsules.

Example 4

Incorporation of a nonionic polyoxyalkylene molecule into the walls of polyurea microcapsules containing Acetochlor using Process (3) above. This experiment demonstrated that a nonionic polyoxyalkylene molecule can be incorporated into microcapsule walls via reaction from the aqueous phase, thereby improving redispersibility of the capsules and affecting the release characteristics of the capsules.

A polyoxyalkylene molecule of the formula $NH_2CH(CH_3)CH_2[PO]_y$—$[EO]_x$—$[PO]_z$—$NH_2$, where PO is propylene oxide, EO is ethylene oxide, y+z=5, and x=39.5 (commercially available as Jeffamine ED2003 from Huntsman) was used to prepare Acetochlor-containing microcapsules. The polyoxyalkylene molecule was dissolved in the aqueous phase. Microcapsule formulations were then prepared as in Example 2 above (but without the sulfonate diamine). The reaction between —$NH_2$ and —OCN at the oil/water interface allowed the polyoxyalkylene groups to chemically bond to the microcapsule wall.

The polyoxyalkylene wall-modified microcapsules showed significant dispersant function. FIG. 1 illustrates that the effect on redispersibility of the polyoxyalkylene wall-modified microcapsules was dependent upon the amount of Jeffamine used. When small amounts of surface modifying compound were used (less than 3.0% in the aqueous phase), the redispersibility of the microcapsules was improved compared to the commercially available Acetochlor capsule suspension ("CS") in both soft and hard water. In contrast, when large amounts of Jeffamine were used (greater than 4.5% in the aqueous phase), the capsules in soft water and hard water became much more difficult to redisperse after settling.

FIG. 2 illustrates the effect of the release rate of Acetochlor from the microcapsules based upon the amount of surface modifying compound used. As shown therein, the release rate was substantially reduced by using 3.0% Jeffamine in the aqueous phase.

Example 5

Incorporation of a polyoxyethylene steric stabilizer into the walls of polyurea microcapsules containing Acetochlor using Process (1) above. This experiment demonstrated that a polyoxyethylene steric stabilizer can be incorporated into microcapsule walls in a formulation containing a free emulsifier and colloid stabilizer.

The steric stabilizer was prepared by the Michael reaction of Jeffamine 1000M with hydroxyethylacrylate (HEA) as described in Example 4 of U.S. Pat. No. 5,153,259. Jeffamine 1000M is available from Huntsman, who gives the structure as $MeOEOl_9PO_3NH_2$, where EO and PO designate respectively —$CH_2CH_2O$— and —$CHMeCH_2O$— groups. Reaction with HEA gives the adduct $MeOEO_{19}PO_3NHCH_2CH_2COCH_2CH_2OH$ in which the —NH— and —OH groups can react with isocyanate groups.

A solution of the above steric stabilizer (0.7 g) and dibutyltin dilaurate (0.1 g) in Acetochlor (20 g) was added at room temperature over 10 minutes to a stirred solution of tolylene 2,4-diisocyanate (4 g) in Acetochlor (20 g). The mixture was heated at 50° C. for 1.5 hours to give the 'oil' phase that was emulsified using a Silverson stirrer into a solution of Reax 1000M (0.7 g) and Tergitol XD (0.7 g) in water (42.9 g) cooled to 8° C. The temperature rose to about 14° C. The emulsion was paddle stirred at 50° C. for 3 hours to give about 5 micron diameter microcapsules.

The capsule suspension was spray dried and the dry powder was tested for redispersibility as described in Example 11.

Example 6

Incorporation of a sulfonate stabilizer into the walls of polyurea microcapsules containing Acetochlor using Process (1) above.

A sulfonate ("SSIPA") polyester polyol was prepared by reacting sodium sulphoisophthalic acid, adipic acid, cyclohexane dimethanol, methoxy-polyethylene glycol (mw 750) and trimethylol propane to give a product having a hydroxyl number in the range of from 150 to 170.

A solution of the above sodium sulfonate polyol (0.2 g) and dibutyltin dilaurate (0.15 g) in Acetochlor (30 g) was added at room temperature over 10 minutes to a stirred solution of tolylene 2,4-diisocyanate (4 g) in Acetochlor (10 g). The mixture was heated at 50° C. for 2 hours then cooled to room temperature and polymethylene polyphenylene-isocyanate (0.13 g) was added to give the oil phase. The oil was emulsified using a Silverson stirrer into a solution of Reax 100M (0.7 g) and Tergitol XD (0.7 g) in water (42.9 g) cooled to 10° C. The emulsion was paddle stirred at 50° C. for 3 hours to give about 5 micron diameter microcapsules which were smooth, spherical, strong with no leakage on drying and were re-suspendable in water.

The capsule suspension was spray dried and the dry powder was tested for redispersibility as described in Example 11.

Example 7

Incorporation of dimethylol propionic acid ("DMPA") into the walls of polyurea microcapsules containing Acetochlor using Process (1) above. This experiment demonstrated that dimethylol propionic acid ("DMPA") [HOCH$_2$CMe(CO$_2$H)CH$_2$OH] can be incorporated into microcapsule walls in a formulation containing a free emulsifier and colloid stabiliser.

A solution of DMPA (0.15 g, 1.12 mmol) and dibutyltin dilaurate (0.15 g) in Acetochlor (5 g) and dimethylacetamide (0.5 g) was added to a stirred solution of tolylene 2,4-diisocyanate (TDI, 2.4 g, 13.79 mmol) in Acetochlor (10 g). The mixture was heated at 55° C. for 2 hours, and then cooled to room temperature when polymethylene polyphenylene-isocyanate (0.15 g) was added to give the 'oil' phase. The oil was emulsified using a Silverson stirrer into a solution of Reax 100M (0.6 g) and Tergitol XD (0.6 g) in water (32.3 g) cooled to 8° C. The emulsion was paddle-stirred at 50° C. for 3 hours, giving robust microcapsules which did not leak on drying and which were re-suspendable in water.

Example 8

Incorporation of dimethylol butyric acid ("DMBA") into the walls of polyurea microcapsules containing Acetochlor using Process (1) above. This experiment demonstrated that DMBA can be incorporated into microcapsule walls in a formulation containing a free emulsifier and colloid stabiliser.

A solution of dimethylol butyric acid (DMBA, 0.15 g) and dibutyltin dilaurate (0.1 g) in Acetochlor (10 g) was added to a stirred solution of tolylene 2,4-diisocyanate (TDI, 2.4 g, 13.79 mmol) in Acetochlor (10 g). The mixture was heated at 55° C. for 2 hours then cooled to room temperature when polymethylene polyphenylene-isocyanate (0.15 g) was added to give the 'oil' phase. The oil was emulsified using a Silverson stirrer into a solution of Reax 100M (0.6 g) and Tergitol XD (0.6 g) in water (32.3 g) cooled to 8° C. The emulsion was paddle stirred at 50° C. for 3 hours to give robust microcapsules that did not leak on drying and were re-suspendable in water.

Example 9

Incorporation of dimethylol propionic acid (DMPA) into the walls of polyurea microcapsules containing lambda-cyhalothrin using Process (1) above. This experiment demonstrated that DMPA-stabilized nanocapsules can be made without the use of free emulsifier.

A stock solution of DMPA-TDI oligomer was prepared by heating a mixture of DMPA (5.60 g, 41.8 mmol), dibutyltin dilaurate (100 mg) and TDI (28.00, 160.8 mmol) in Solvesso 200 (50.02 g) at 85° C. for about 7 hours under nitrogen.

The above stock solution (6.67 g; containing 0.447 g DMPA, 2.23 g TDI and 3.99 g solvent) was added to a solution of lambda-cyhalothrin (48.90 g), TDI (8.05 g) and polymethylene polyphenyleneisocyanate (0.396 g) in Solvesso 200 (36.03 g), and the mixture was cooled to 8° C. The chilled oil was roughly emulsified into a solution of Reax 100M (0.21 g) and sodium hydroxide (0.13 g) in water (97.4 g) at 8° C. The chilled emulsion was passed through a Microfluidics microfluidizer and paddle stirred at 50° C. for 3 hours giving nanocapsules having a mean diameter of 534 nm.

Example 10

Self-stabilized dimethylol propionic acid (DMPA) modified polyurea microcapsules containing lambda-cyhalothrin made by Process (1) above. This experiment demonstrated that DMPA self-stabilized microcapsules can be made without the use of free emulsifier or colloid stabiliser.

The stock solution from Example 9 (6.67 g; containing 0.447 g DMPA, 2.23 g TDI and 3.99 g solvent) was added to a solution of lambda-cyhalothrin (48.90 g), TDI (8.05 g) and polymethylene polyphenyleneisocyanate (0.396 g) in Solvesso 200 (36.03 g) and the mixture was cooled to 8° C. The chilled oil was roughly emulsified by shaking into a solution of sodium hydroxide (0.13 g) in water (97.4 g) at 8° C. The chilled pre-emulsion was passed through a Microfluidics microfluidiser and paddle stirred at 50° C. for 3 hours giving self-stabilized microcapsules having a mean diameter of 1.8 µm.

Example 11

Spray Drying General Procedure

The wall composition of the spray dried samples is cross-referenced in Table 1. Example 1 in Table 1 pertains to Acetochlor capsules of similar wall weights and prepared by the same in situ polymerization method, but which did not contain any surface modifying compounds.

A suspension of the test microcapsules (2.25 g solids) in a solution of polyacrylic acid (0.25 g of molecular weight 500) and Reax 85A (0.075 g) in water (45 ml) was spray dried using a Buchi Mini Spray Drier Unit (Model 190) with the inlet at about 140° C. and the outlet at about 70° C. The dilute capsule suspension was forced through the nozzle head by a nitrogen flow. The product was usually a free flowing dry powder apart from those from microcapsules modified with DMPA and DMBA which adhered very strongly to the glass walls of the spray drier.

Redispersibility Testing

The redispersibility of the spray dried products into water was compared against Acetochlor capsules of similar wall weights and prepared by the same in situ polymerisation method but which did not contain any surface modifying compounds. The dried powder (5 mg) was added to 3 ml of water contained in a glass vial. The vial was sealed and sharply inverted 10 times. A sample of the suspension was removed and examined under the microscope and by a Coulter LS130 particle size analyser. The redispersibility to single particles was qualitatively assessed relative to the reference non-modified capsules (rated +++). Redispersion for capsules from Example 5 (J1000M-HEA) was appreciably better, while that from Example 6 (SSIPA polyol) was substantially better in that it was estimated that more than 95% of the sample was present as single microcapsules.

TABLE 1

Redispersibility of Spray Dried Microcapsules

| Spray dry Example | Example - | Sample Surface modified | Relative amount of single microcapsules |
|---|---|---|---|
| 1 | Reference | None | +++ |
| 2 | 5 | JM1000-HEA | ++++ |
| 3 | 6 | SSIPA polyol | +++++ |
| 4 | 7 | DMPA | Not tested |
| 5 | 8 | DMBA | Not tested |

Example 12

Incorporation of a polyoxyethylene steric stabiliser into the walls of polyurea microcapsules containing lambda-cyhalothrin or tefluthrin using Process (1) above. This experiment demonstrated that polyoxyethylene stabilised microcapsules can be made without the use of free emulsifier.

Methoxy polyethylene glycol [MeO(EO)$_n$OH] with an average molecular weight of 750 ("MeOPEG 750") was reacted with polymethylenepolyphenylene isocyanate ("PMPPI") in a 1:2 molar ratio to form a surface modifying intermediate. MeOPEG 750 and PMPPI were heated in methylene chloride at 35° C. for 6 hours, monitoring the reaction by infra-red spectroscopy. The progress of the reaction was indicated by the diminishing of the isocyanate peak at 2267 cm$^{-1}$ and the increasing of the polyurethane (—O—CO—NH—) carbonyl peak at 1729 cm$^{-1}$. After reaction, the methylene chloride was evaporated.

The MeOPEG 750-PMPPI modified oligomer was then added to an organic phase comprising a solution of lambda-cyhalothrin or tefluthrin, tolylene diisocyanate and additional PMPPI in Solvesso 200, according to the compositions outlined in Table 2. The oil was emulsified into a solution of Lomar D (0.7 g) in water (37.8 g) using a Silverson stirrer, and the emulsion was paddle stirred at 55° C. for 3 hours to give robust 3.8-4.1 µm microcapsules that did not leak on drying. Under the preparative conditions used these capsules are smaller than would normally be expected in the absence of an external emulsifier, indicating that the MeOPEG 750-PMPPI modified oligomer has emulsification properties. Alternatively the emulsion was passed through a Microfluidics microfluidiser prior to heating to give robust capsules of 0.9-1.0 µm.

TABLE 2

| Composition of organic phase | | |
|---|---|---|
| Lambda-cyhalothrin or tefluthrin (grams) | 7.0 | 7.0 |
| MeOPEG 750-PMPPI (grams) | 1.46 | 0.73 |
| TDI (grams) | 0.79 | 0.79 |
| PMPPI (grams) | 1.60 | 1.99 |
| Solvesso 200 (grams) | 20.64 | 21.0 |

Example 13

Self-stabilised MeOPEG 750 modified polyurea microcapsules containing lambda-cyhalothrin or tefluthrin made by Process (1) above. This experiment demonstrated that MeOPEG 750 self-stabilised microcapsules can be made without the use of a free emulsifier or colloid stabiliser.

The MeOPEG 750-PMPPI oligomer from Example 12 (2.19 g) was added to a solution of lambda-cyhalothrin or tefluthrin (7.0 g), tolylene diisocyanate (0.79 g) and additional PMPPI (1.23 g) in Solvesso 200 (20.29 g). This oil was emulsified into 38.5 g water using a Silverson stirrer, and the emulsion was paddle stirred at 55° C. for 3 hours to give robust self-stabilised microcapsules, which did not break on drying.

Example 14

Incorporation of a hydrophilically modified aliphatic isocyanate into the walls of polyurea microcapsules containing lambda-cyhalothrin using Process (1) above. This experiment demonstrated that a hydrophilically modified aliphatic isocyanate can be used to form microcapsule walls in the absence of additional unmodified isocyanate.

Bayhydur 3100 is a hydrophilically modified aliphatic polyisocyanate based on hexamethylene diisocyanate (HDI), commercially available from Bayer.

Bayhydur 3100 (2.0 g) was added to an organic phase comprising a solution of lambda-cyhalothrin (5.0 g) in Solvesso 200 (13.0 g). This oil was emulsified into a solution of Lomar D (1.1 g) in water (26.2 g), and the emulsion was paddle stirred whilst a 10% aqueous solution of diethylenetriamine (2.70 g) was added. Upon reaction of the amine with Bayhydur 3100, robust microcapsules were formed which did not leak upon drying.

Example 15

Tefluthrin-containing polyurea microcapsules containing both a non-ionic polyoxyalkylene modifier and an anionic sulfonate diamine modifier made by Process (3) above. This experiment demonstrated that a non-ionic polyoxyalkylene modifier and an anionic sulfonate diamine modifier could be combined in the walls of microcapsules containing tefluthrin.

Jeffamine ED2003 is a commercially available polyoxyalkylene molecule as described in Example 4, and Poly-EPS 520-Na is a commercially available sulfonate diamine as described in Example 2. An organic phase was prepared by dissolving tefluthrin (38.4 g), tolylene diisocyanate (8.36 g) and polymethylenepolyphenylene isocyanate (0.28 g) in Aromatic 100 (31.43 g). This oil was emulsified into a solution of Tergitol XD (9.86 g), Lomar D (0.16 g) and Poly-EPS 520-Na (1.8 g) in water (61.81 g) using a Silverson stirrer. The emulsion was paddle stirred at 45° C. for a total of 2.5 hours, with Jeffamine ED2003 (0.89 g) being added dropwise shortly after the heating had begun to give nanocapsules with a mean particle size of 0.4 µm.

Example 16

Incorporation of a cationic quaternary ammonium alkylamine into the walls of polyurea microcapsules containing lambda-cyhalothrin using Process (3) above. This experiment demonstrated that cationic quaternary ammonium alkylamine stabilised microcapsules can be made without the use of a free colloid stabiliser.

(2-Aminoethyl) trimethylammonium chloride hydrochloride is available from Aldrich and will be referred to henceforth as "AETMA Cl". An organic phase was prepared by dissolving lambda-cyhalothrin (5.0 g), tolylene diisocyanate (0.56 g) and polymethylenepolyphenylene isocyanate (1.69 g) in Solvesso 200 (15.25 g). This oil was emulsified into a solution of Tergitol XD (0.28 g) and optionally AETMA Cl (0.55 g) in water (26.67 g) using a Silverson stirrer. The emulsion was paddle stirred at 55° C. for 3 hours, with the results as indicated below.

| Presence of cationic wall modifying agent | % protective colloid | State of microcapsule dispersion | Microcapsule particle size (μm) |
|---|---|---|---|
| Yes | 0% | Dispersed capsules with good wall strength | 39 |
| No | 0% | Agglomerated during cook | — |

These results reflect the dispersant function of AETMA Cl when incorporated into the microcapsule wall.

Example 17

Lambda-cyhalothrin containing polyurea microcapsules containing both a cationic quaternary ammonium alkylamine modifier and a non-ionic polyoxyethylene steric modifier made using a combination of Processes (1) & (3) above. This experiment demonstrated that a cationic quaternary ammonium alkylamine and a non-ionic polyoxyethylene modifier can be combined in the walls of microcapsules containing lambda-cyhalothrin.

The MeOPEG 750-PMPPI modified oligomer from Example 12 was added to an organic phase comprising a solution of lambda-cyhalothrin, tolylene diisocyanate and additional PMPPI in Solvesso 200. This oil was emulsified into water or an aqueous solution of AETMA Cl using a Silverson stirrer, and the emulsion was paddle stirred at 55° C. for 3 hours (details of compositions given in Table 3 below). The samples containing AETMA Cl gave robust microcapsules of 5.6-7.1 μm (compositions 17a and 17b), which did not leak on drying. Again the dispersant function of AETMA Cl is reflected, with robust capsules being formed containing 16.8% MeOPEG 750 in the presence of 4% aq. AETMA Cl, whereas increasing the MeOPEG 750 concentration to 22.4% is insufficient to produce stabilised microcapsules (composition 17c) in the absence of AETMA Cl (MeOPEG 750 concentration expressed as a percentage of the wall material).

TABLE 3

Composition of microcapsules containing AETMA Cl and MeOPEG 750 modifiers

| Composition | 17a | 17b | 17c |
|---|---|---|---|
| Lambda-cyhalothrin (grams) | 5.0 | 5.0 | 7.0 |
| MeOPEG 750-PMPPI (grams) | 1.56 (gives 33.6% MeOPEG) | 0.78 (gives 16.8% MeOPEG) | 1.46 (gives 22.4% MeOPEG) |
| TDI (grams) | 0.56 | 0.56 | 0.79 |
| PMPPI (grams) | 0.88 | 1.29 | 1.60 |
| Solvesso 200 (grams) | 14.50 | 14.87 | 20.65 |
| AETMA Cl (grams) | 0.55 g (gives 2% aq) | 1.10 (gives 4% aq) | 0 |
| Water (grams) | 26.95 | 26.40 | 38.5 |
| State of microcapsule dispersion | Dispersed capsules with good wall strength | Dispersed capsules with good wall strength | Agglomerated during cook |

Example 18

Lambda-cyhalothrin containing polyurea microcapsules containing both a cationic quaternary ammonium diol modifier and a non-ionic polyoxyethylene steric modifier made by Process (1) above. This experiment demonstrated that a cationic quaternary ammonium diol and a non-ionic polyoxyethylene steric stabiliser can be combined in the walls of microcapsules containing lambda-cyhalothrin.

Benzoxonium chloride is supplied as a 40% aqueous solution by Laporte and has the structure shown below. The diol was extracted by heating to 60° C. to allow most of the water to evaporate, and then the remaining water was removed by azeotropic distillation with toluene.

The extracted benzoxonium chloride was reacted with isophorone diisocyanate (IPDI) in a 1:5 molar ratio of diol:isocyanate to form a chain extended surface modifying agent. Benzoxonium chloride and IPDI were refluxed in toluene at 125° C. for 8.5 hours under nitrogen (in the presence of a catalytic quantity of dibutyltin dilaurate), monitoring the reaction by infra-red spectroscopy. The progress of the reaction was indicated by the diminishing of the isocyanate peak at 2260 cm$^{-1}$ and the increasing of the polyurethane (—O—CO—NH—) carbonyl peak at 1725 cm$^{-1}$. After reaction the toluene was removed by rotary evaporation.

The benzoxonium chloride-IPDI modified oligomer and the MeOPEG 750-PMPPI modified oligomer described in Example 12 were added to an organic phase comprising a solution of lambda-cyhalothrin and additional PMPPI in Solvesso 200, according to the compositions outlined in Table 4. The oil was emulsified into 27.5 g water using a Silverson stirrer, and the emulsion was paddle stirred at 55° C. for 3 hours to give robust 3.4-5.0 μm microcapsules, which did not leak on drying.

TABLE 4

| Composition of organic phase | | |
|---|---|---|
| Lambda-cyhalothrin (grams) | 5.0 | 5.0 |
| MeOPEG 750-PMPPI (grams) | 1.56 | 1.03 |
| Benzoxonium chloride-IPDI (grams) | 0.76 | 1.52 |
| PMPPI (grams) | 0.88 | 0.60 |
| Solvesso 200 (grams) | 14.3 | 14.35 |

Example 19

Lambda-cyhalothrin containing polyurea microcapsules containing both quaternised Bisomer PTE40 and a non-ionic polyoxyethylene steric stabiliser made by Process (1) above. This experiment demonstrated that quaternised Bisomer PTE40 and MeOPEG 750 can be combined in the walls of microcapsules containing lambda-cyhalothrin.

Bisomer PTE40 (available from Inspec) is an amino oxyethylene diol with the structure shown below. The amino group was quaternised by reaction with a 2-fold excess of methyl iodide in diethyl ether. The solution was stirred at 35° C. for 5.5 hours, by which time the quaternised molecule had phase separated from the solvent which was removed by rotary evaporation. NMR spectroscopy confirmed the reaction between Bisomer PTE40 and methyl iodide.

HO~O~N(~O~OH)(C6H4-CH3)  + MeI →

The quaternised Bisomer PTE40 was reacted with isophorone diisocyanate (IPDI) in a 1:5 molar ratio to form a chain extended surface modifying agent. Quaternised Bisomer PTE40 and IPDI were refluxed in toluene at 125° C. for 15 hours under nitrogen (in the presence of a catalytic quantity of dibutyltin dilaurate), monitoring the reaction by infra-red spectroscopy. The progress of the reaction was indicated by the diminishing of the isocyanate peak at 2260 cm$^{-1}$ and the increasing of the polyurethane (—CO—NH) carbonyl peak at 1727 cm$^{-1}$. After reaction the toluene was removed by rotary evaporation.

The quaternised Bisomer PTE40-IPDI modified oligomer and the MeOPEG 750-PMPPI modified oligomer from Example 12 were added to an organic phase comprising a solution of lambda-cyhalothrin and additional PMPPI in Solvesso 200, according to the compositions outlined in Table 5 below. The oil was emulsified into 27.5 g water using a Silverson stirrer, and the emulsion was paddle stirred at 55° C. for 3 hours to give robust microcapsules which did not leak upon drying.

TABLE 5

| Composition of organic phase | | |
|---|---|---|
| Lambda-cyhalothrin (grams) | 5.0 | 5.0 |
| MeOPEG 750-PMPPI (grams) | 1.56 | 1.03 |
| Quaternised Bisomer PTE40-IPDI (grams) | 0.75 | 1.50 |
| PMPPI (grams) | 0.88 | 0.60 |
| Solvesso 200 (grams) | 14.31 | 14.37 |

Example 20

Incorporation of a phosphonic acid-containing polyester (ITC 1082) into the walls of polyurea capsules containing lambda-cyhalothrin made by Process (1) above. This experiment demonstrated that a phosphonic acid-containing polyester can be incorporated into the walls of capsules containing lambda-cyhalothrin in the absence of an external colloid stabiliser.

ITC 1082 is a phosphonic acid-containing polyester supplied by Rhodia with the structure shown below.

$m = 1.2; n = 2.4$ $m=1.2; n=2.4$

ITC1082 was reacted with isophorone diisocyanate (IPDI) in a 1:10 molar ratio to form a chain extended surface modifying agent. ITC1082 (4 g) and IPDI (10 g) were heated in Solvesso 200 (15.15 g) at 105° C. under nitrogen for 7 hours, monitoring the reaction by infra-red spectroscopy. The progress of the reaction was indicated by the diminishing of the isocyanate peak at 2260 cm$^{-1}$ and the increasing of the polyurethane (—O—CO—NH—) carbonyl peak at 1737 cm$^{-1}$.

The ITC1082-IPDI modified oligomer (1.63 g) was then added to an oil phase comprising a solution of lambda-cyhalothrin (5 g) and polymethylenepolyphenylene isocyanate (1.69 g) in Solvesso 200 (14.18 g). This oil was emulsified into a solution of Tergitol XD (0.28 g) in water (27.22 g) using a Silverson stirrer, and the emulsion was paddle stirred for 3 hours at 55° C. to give robust 5 μm microcapsules which did not leak upon drying. This illustrates the dispersing and/or colloid stabilising properties of ITC1082 when incorporated into microcapsule walls.

Example 21

Self-stabilised ITC1082 modified polyurea microcapsules containing lambda-cyhalothrin made by Process (1) above. This experiment demonstrated that self-stabilised microcapsules can be prepared with the phosphonic acid-containing polyester ITC1082 incorporated into the capsule walls in the absence of external emulsifier or colloid stabiliser.

The ITC1082-IPDI modified oligomer from Example 20 (1.63 g) was added to an oil phase comprising a solution of lambda-cyhalothrin (5 g) and polymethylenepolyphenylene isocyanate (1.69 g) in Solvesso 200 (14.18 g). This oil was emulsified into 27.5 g water using a Silverson stirrer, and the emulsion was paddle stirred for 3 hours at 55° C. to give robust 14 μm self-stabilised microcapsules which did not leak upon drying.

Example 22

Biological efficacy of surface modified polyurea capsules containing lambda-cyhalothrin against aphids—contact/residual test. These experiments demonstrated that the introduction of an anionic sulfonate diamine modifier into the walls of polyurea capsules containing lambda-cyhalothrin can alter the release rate of the active ingredient, resulting in increased bioefficacy.

A series of four contact/residual bioassays were conducted to evaluate the aphicidal activity of a range of surface modified capsules against R2 *Myzus persicae*. A mixed age population of R2 *Myzus persicae* was tested and mortality was assessed after three days. The capsules tested were based on a formulation containing 25% lambda-cyhalothrin with a 10% capsule wall (3:1 polymethylenepolyphenylene isocyanate:tolylene diisocyanate), and contained 0, 2.5%, 3.7% or 5% Poly-EPS 520-Na modifier (expressed as a percentage of the aqueous phase). All capsules had a mean particle size in the range 0.7-1.1 μm. The mean LC50 and LC90 values from the four tests are given in Table 6 below.

TABLE 6

Mean LC50 & LC90 values of surface modified lambda-cyhalothrin capsules

| % Poly-EPS 520-Na | Mean LC50 | Mean LC90 |
|---|---|---|
| 0 | 77.423 | 215.315 |
| 2.5 | 13.882 | 38.836 |
| 3.7 | 17.019 | 47.411 |
| 5 | 19.202 | 53.279 |

These results clearly demonstrate that much higher aphicidal activity is observed when Poly-EPS 520-Na is incorporated into the capsule wall than would normally be expected for a capsule with a 3:1 PMPPI:TDI wall.

Example 23

Soil plate movement studies on surface modified polyurea capsules containing tefluthrin. These experiments demonstrated that incorporating anionic or steric modifiers into the walls of capsules containing tefluthrin could result in increased movement through soil relative to capsules not so modified.

Tefluthrin microcapsules (10% wall on microcapsules; 45% solids) modified by either DMPA, Poly-EPS 520-Na (anionic modifiers) or MeOPEG 750 (steric modifier) were tested for soil movement using the test described below. The DMPA and MeOPEG 750-modified capsules were prepared using Process 1, and the Poly-EPS 520-Na modified capsules were prepared using Process 3. These capsules were compared to equivalent microcapsules which did not contain any surface modifying compounds.

1 mm sieved soil was packed into metal plates (30×5×0.5 cm; and marked at 2, 3, 4, 5, 10, 15, and 20 cm intervals) to which 8 cm muslin wicks were then fixed between the 0-2 cm line positions. The top and bottom of each plate was rested at an incline of 11° over the edges of 250 ml reservoirs, such that the wick was suspended in the upper reservoir, all being contained within an enclosed tank. The tank and the upper reservoir were charged with 0.01M $CaCl_2$ solutions. The solution in the upper reservoir was drawn by capillary action up the wick and thence eluted down the plate to be collected in the lower reservoir. When the plate was fully wetted 10×10 μL of 1 mg/mL of the test composition was applied across the 2 cm line and the plate was eluted with 200 mL of the 0.01M $CaCl_2$ solution from the upper reservoir.

The plate was carefully removed from the tank and sectioned up according to the markings. The sections were placed in a 50 ml centrifuge tubes, weighed and 30 ml of Acetone was added. The resulting slurry was mechanically shaken for approximately 3 hours before being centrifuged at 3000 rpm for 5 minutes. An aliquot of the supernatant solution was removed, analysed by gas chromatography, and compared with previously made standards to obtain recovery.

The following Tables show the normalised percentage recoveries of tefluthrin from the soil taken from the marked intervals (left hand column) on the plates. The top row of the Table gives the microcapsule size and the type and amount of surface modifying agent incorporated.

TABLE 7

Soil movement of tefluthrin in capsules modified by dimethylol propionic acid (DMPA; concentrations expressed as % of wall material)

| Distance moved down plate | 2.8 μm 0% DMPA | 3.5 μm 2% DMPA | 3.5 μm 4% DMPA | 4.1 μm 6% DMPA | 0.7 μm 0% DMPA | 1.25 μm 2% DMPA | 1.05 μm 4% DMPA | 1.12 μm 6% DMPA |
|---|---|---|---|---|---|---|---|---|
| 0-2 cm | 15 | 4 | 12 | 6 | 10 | 4 | 6 | 5 |
| 2-3 cm | 69 | 49 | 51 | 51 | 56 | 57 | 67 | 62 |
| 3-4 cm | 9 | 21 | 16 | 20 | 16 | 24 | 18 | 22 |
| 4-5 cm | 3 | 11 | 8 | 10 | 8 | 7 | 4 | 7 |
| 5-10 cm | 6 | 15 | 13 | 13 | 10 | 7 | 4 | 4 |

These results show that tefluthrin is moved further through the soil when it is contained in microcapsules with anionic DMPA molecules incorporated into the capsule wall than when contained in similar but unmodified capsules.

TABLE 8

Soil movement of tefluthrin in capsules modified by Poly-EPS 520-Na
(EPS-520 concentrations expressed as % of aqueous phase)

| Distance moved down plate | 2.8 μm 0% EPS-520 | 3.8 μm 2.5% EPS-520 | 3.9 μm 3.7% EPS-520 | 3.6 μm 5% EPS-520 | 0.7 μm 0% EPS-520 | 0.6 μm 2.5% EPS-520 | 0.6 μm 3.7% EPS-520 | 0.6 μm 5% EPS-520 |
|---|---|---|---|---|---|---|---|---|
| 0-2 cm | 15 | 4 | 4 | 24 | 10 | 7 | 3 | 15 |
| 2-3 cm | 69 | 54 | 53 | 52 | 56 | 53 | 28 | 35 |
| 3-4 cm | 9 | 20 | 18 | 11 | 16 | 22 | 23 | 15 |
| 4-5 cm | 3 | 9 | 11 | 4 | 8 | 10 | 17 | 9 |
| 5-10 cm | 3 | 9 | 10 | 5 | 6 | 7 | 22 | 19 |
| 10-15 cm | 1 | 2 | 2 | 1 | 2 | 1 | 7 | 4 |
| 15-20 cm | 1 | 1 | 1 | 1 | 1 | 0 | 0 | 1 |
| 20-30 cm | 1 | 1 | 1 | 1 | 1 | 0 | 0 | 1 |

These results show that tefluthrin is moved further through the soil when it is contained in microcapsules with anionic Poly-EPS 520-Na molecules incorporated into the capsule wall than when contained in similar but unmodified capsules.

TABLE 9

Soil movement of tefluthrin in capsules modified by MeOPEG 750
(MeOPEG concentrations expressed as % of wall material)

| Distance moved down plate | 2.8 μm 0% MeOPEG | 4.1 μm 11.2% MeOPEG | 3.8 μm 22.4% MeOPEG | 3.3 μm 33.6% MeOPEG | 0.7 μm 0% MeOPEG | 0.9 μm 11.2% MeOPEG | 0.9 μm 22.4% MeOPEG | 1 μm 33.6% MeOPEG |
|---|---|---|---|---|---|---|---|---|
| 0-2 cm | 15 | 4 | 4 | 4 | 10 | 33 | 3 | 5 |
| 2-3 cm | 69 | 51 | 36 | 36 | 56 | 44 | 62 | 43 |
| 3-4 cm | 9 | 23 | 24 | 24 | 16 | 13 | 26 | 20 |
| 4-5 cm | 3 | 10 | 17 | 16 | 8 | 5 | 5 | 16 |
| 5-10 cm | 3 | 10 | 17 | 17 | 6 | 4 | 3 | 13 |
| 10-15 cm | 1 | 1 | 2 | 1 | 2 | 1 | 1 | 1 |
| 15-20 cm | 1 | 0 | 1 | 1 | 1 | 0 | 0 | 1 |
| 20-30 cm | 1 | 0 | 0 | 0 | 1 | 0 | 0 | 0 |

These results show that tefluthrin is moved further through the soil when it is contained in microcapsules with MeOPEG 750 molecules incorporated into the capsule wall than when contained in similar but unmodified capsules.

Example 24

Biological efficacy of surface modified tefluthrin-containing polyurea capsules against corn rootworm—zone of protection test. This experiment demonstrated that increased movement of tefluthrin through soil in capsules surface modified by DMPA or Poly-EPS 520-Na can be translated into enhanced bioefficacy against soil-borne pests.

The tefluthrin (soil insecticide) capsules modified by DMPA or Poly-EPS 520-Na from Example 23 were screened in a zone of protection test against corn rootworm (*Diabrotica undecimpunctata undecimpunctata*), with the results being compared to those of the commercial standard 3% tefluthrin granular formulation. Test method: Tefluthrin formulations were applied at one specific spot in the middle, and at 1.5 in below the surface of soil in a 19.5 cm container; this application point is known as the point source. The amount applied was equivalent to the amount of product applied in 19.5 cm of a row for an application rate of 5 oz./1000 row feet (4.25 g a.i./1000 ft.). The soil was brought to 15% soil moisture (by weight) after application, and the tub was covered. The closed container was allowed to equilibrate for four weeks at 25° C. before the seeds were planted.

Corn seeds were soaked in water for 24 hours and then germinated on paper towels for 24 hours. These seeds were planted at one centimetre spacing from the point source in a spiral pattern. Seeds were planted at a depth of 1.5 inches to simulate drill planting. Additionally, 200 μl of agar solution containing Diabrotica eggs (1 ml of eggs in 27 ml of 0.18% agar solution≈50 eggs/200 μl) were pipetted into each hole with the corn seed, after which, the holes were filled with soil. Containers were maintained in the glasshouse until the time for assessment.

A linear rating system developed by Dr. James Oleson at Iowa State University, and summarised below, was used to grade root damage.
Rating Node-Injury Scale or Oleson's Linear Scale
0.0—No feeding damage (lowest rating that can be given)
1.00—One node (circle of roots), or the equivalent of an entire node, eaten back to within ~one inch of the stalk
2.00—Two nodes eaten
3.00—Three or more nodes eaten (highest rating that can be given)

Decimal numbers were employed to note a percentage of the node missing, i.e. 1.50=1½ nodes eaten, 0.25=¼ of one node eaten, etc. This scale was modified for evaluating seedling corn by including in the evaluation the stem of the plant from the seed to the soil surface and from the soil surface to about 3 cm above the ground. Each are counted as nodes because these are areas that experience intense feeding and become necrotic and collapse from damage. These two nodes are evaluated on percentage damage.

Results

The mean ratings using the linear scale are given in Table 10 below (this takes into account the amount of damage observed at 1 cm intervals over a distance of 1-8 cm from the point source).

TABLE 10

Mean damage observed
using linear scale root ratings - arcsine transformation (x/3)
(means followed by the same letter are not statistically different)

| Sample details | Mean rating |
|---|---|
| 0.6 μm; 2.5% EPS-520 | 0.57 a |
| 0.6 μm; 3.7% EPS-520 | 0.41 ab |
| 0.6 μm; 5% EPS-520 | 0.41 ab |
| 1.25 μm; 2% DMPA | 0.20 c |
| 1.05 μm; 4% DMPA | 0.25 bc |
| 1.12 μm; 6% DMPA | 0.19 c |
| Tefluthrin 3G | 0.42 ab |

These results show that the tefluthrin capsules modified by Poly EPS-520 are comparable with, and by DMPA are significantly more active than, the commercial 3G standard.

Example 25

Biological efficacy of sulphonate (Poly EPS 520) and steric (Jeffamine ED2003) surface modified tefluthrin-containing polyurea capsules against corn rootworm. These experiments demonstrated that increased movement of tefluthrin through soil in capsules surface modified by Poly-EPS 520-Na or Jeffamine ED2003 can be translated into enhanced bioefficacy against soil-borne pests.

These tests were designed to screen the relative mobility in soil of Tefluthrin (soil insecticide) contained in microcapsules and nano-capsules with and without surface modification. The following formulations were tested [all microcapsules* had the same weight percent wall (7.5%) and crosslink density (PMPPI:TDI 1:30) all nanocapsules* had the same weight percent wall (11%) and crosslink density (PMPPI:TDI 1:30)]:

| formulation* | capsule size (μm) | surface modification |
|---|---|---|
| microcapsules | | |
| A | 2.7 | none |
| B | 3.2 | sulphonate (polyEPS-520Na) |
| C | 3.1 | (EO)x (Jeffamine ED2003) |
| nanocapsules | | |
| D | 0.27 | none |
| E | 0.23 | sulphonate (polyEPS-520Na) |
| F | 0.27 | (EO)x (Jeffamine ED2003) |

*Formulations were made via process described in U.S. Pat. No. 4,285,720 by in situ interfacial condensation of poly(methylenepolyphenylene isocyanate) (PMPPI) and tolylene diisocyanate (TDI) at 50° C.

Example 25a

Zone of Protection Test: The test procedure was similar to that described for Example 24. The extent of damage by corn root worms was assessed one month after planting as a function of plant heights and the rating system developed by Dr. James Oleson at Iowa State University.

Results:

The distances from the point source at which damage began are collected in the following Table which shows that Formulation E (nanocapsules with sulphonate surface modification) gave the highest zone of protection in this test.

| Formulation | Distance (cm) from centre where damage begins (½ node destroyed) |
|---|---|
| A | 4.75 |
| B | 5.61 |
| C | 3.37 |
| D | 6.4 |
| E | 6.75 |
| F | 5.18 |

Example 25b

Root Box Test (simulation of seed treatment on corn seed). For this test 1 mL of the test formulation was pipetted on to each of 10 seeds sown in a large root box enclosed in a greenhouse. The trial was infested on days 1 and 14 at a level of 600 eggs/ft to more closely simulate the field by allowing for a variety of growth stages of rootworm to be attacking the roots at the same time. At infestation, Diabrotica eggs were suspended in 0.18% agar solution and pipetted into 1-1.5" deep divots approximately 2-3" from the base of the plants on both sides of the row. The divots were covered with loose soil, and the test was irrigated after infesting to keep the eggs from desiccating. Due to a pipette problem, half of the fourth replication was infested at 10 times the specified level at first infestation.

However, statistical analysis indicates that the fourth replication did not have an inordinately large amount of root damage. The rating methods used in this trial are the linear rating system developed by Dr. James Oleson at Iowa State University.

| Formulation | number nodes destroyed on roots of corn plants |
|---|---|
| *D | 0.617 |
| *E | 0.316 |
| *F | 0.557 |
| **Tefluthrin 3G in furrow | 0.485 (farmers will tolerate 0.5) |
| **Tefluthrin 3G-T band (applied in bands on both sides of furrow) | 0.155 |
| Untreated check | 1.830 (plant in danger of falling over) |

*Tefluthrin microcapsule formulations pipetted on to seed
**Tefluthrin 3G-commercial Tefluthrin 3% granular formulation (montmorillonite clay) applied dry Formulation E (nanocapsule with sulphonate surface modification) which was applied directly to seed again gave the highest soil mobility in this seed treatment simulation test. It was superior to the commercial standard granule distributed in furrow but not quite as good as the commercial standard granule distributed in bands on either side of the furrow.

Example 26

Examples 26a-1

Incorporation of a polyoxyethylene modifying agent into the walls of aminoplast capsules. These experiments demonstrated that a polyoxyethylene modifying agent (Jeffamine 1000M) can be reacted with an etherified urea-formaldehyde resin (Beetle 80) to give a product with surface active properties which can be incorporated into the walls of lambda-cyhalothrin containing aminoplast microcapsules.

Example 26a

Incorporation of a polyoxyethylene modifying agent into an etherified urea-formaldehyde resin.

Beetle 80 (9.0 g), Jeffamine 1000M (0.5, 1.0 or 2.0 g) and p-toluenesulphonic acid (0.03 g) were dissolved in toluene and refluxed for 6.5 h. The mixture was cooled and filtered to remove undissolved p-toluenesulphonic acid, and the toluene was evaporated to give an oily liquid.

Jeffamine 1000M [MeOEO 19PO3NH2 where EO and PO designate —CH2CH2O— and —CHMeCH2O— groups respectively] is available from Huntsman. The etherified ureaformaldehyde resin Beetle 80 is available from American Cyanamid; 94% of the methylol groups in the prepolymer have been etherified with n-butanol.

Examples 26b-g

Formation of Stable Emulsions

These experiments demonstrated that the modified resin from Example 26a has enhanced emulsification properties.

Emulsion-in-water (EW) formulations were prepared using the modified resin from Example 26a, and were compared with EWs of the same composition but in which the Jeffamine 1000M and prepolymer had not been reacted prior to emulsification. Compositions, chosen to reflect typical precursor mixtures for microcapsules, are detailed in the table below.

The modified resin (or Beetle 80 and Jeffamine 1000M) and pentaerythritol tetrakis 3-mercaptopropionate (otherwise known as Q43) were dissolved in Solvesso 200 (aromatic solvent available from Exxon) to give an organic phase (oil) that was emulsified into a solution of Petro BAF (a sodium alkyl naphthalene sulphonate available from Cognis) in water using a Silverson mixer. The pH of the emulsions was adjusted to 2.0-2.2 by the drop wise addition of a 10:1 dilution of sulphuric acid.

| Example | 26b | 26c | 26d | 26e | 26f | 26g |
|---|---|---|---|---|---|---|
| Solvesso 200 (grams) | 31.09 | 31.09 | 26.74 | 26.74 | 17.34 | 17.34 |
| Q43 (grams) | 0.82 | 0.82 | 0.71 | 0.71 | 0.46 | 0.46 |
| Beetle 80 (grams) | 7.36 | 7.36 | 6.97 | 6.97 | 4.76 | 4.76 |
| Jeffamine 1000M (grams) | 1.64 | 1.64 | 0.77 | 0.77 | 0.26 | 0.26 |
| Petro BAF (grams) | 0.03 | 0.03 | 0.03 | 0.03 | 0.02 | 0.02 |
| Water (grams) | 40.94 | 40.94 | 35.21 | 35.21 | 22.84 | 22.84 |
| Pre-reaction of Beetle 80 & Jeffamine 1000M | Yes | No | Yes | No | Yes | No |
| EW stable upon acidification | Yes | No | Yes | No | Yes | No |

The emulsions prepared using the modified resins (Examples 26b, d and f) were stable for several days at ambient temperature, whereas those prepared using Beetle 80 and Jeffamine 1000M that had not been pre-reacted (Examples 26c, e and g) broke down immediately upon acidification. This indicates that the modification of Beetle 80 with Jeffamine 1000M results in the generation of a product with enhanced emulsification and colloid stabilising properties.

Examples 26h-l

These experiments demonstrated that the modified resin from Example 26a can be incorporated using Process (1) above into the walls of lambda-cyhalothrin containing microcapsules in the presence of a free colloid stabiliser, but without the use of a free emulsifier.

Capsule suspension (CS) formulations were prepared according to the table below in which the modified resin described in example 26a was incorporated into the microcapsule walls. Lambda-cyhalothrin, Q43 and the modified resin were dissolved in Solvesso 200 to give the internal oil phase. Petro BAF and Lomar D (a sodium naphthalene sulphonate available from Cognis) were dissolved in water, and the pH of this solution was reduced to 2.0-2.2 by drop wise addition of a 10:1 dilution of sulphuric acid to give the continuous aqueous phase. The oil phase was emulsified into the aqueous phase, then the emulsion was paddle stirred at 55° C. for 3 hours.

In each case spherical capsules were produced with good wall strength and integrity (capsule sizes in the range 13-18?m).

| Example | 26h | 26i | 26j | 26k | 26l |
|---|---|---|---|---|---|
| lambda-cyhalothrin (grams) | 5.00 | 5.00 | 5.00 | 5.00 | 5.00 |
| Solvesso 200 (grams) | 8.04 | 8.04 | 8.04 | 8.02 | 7.91 |
| Q43 (grams) | 0.38 | 0.38 | 0.38 | 0.94 | 0.94 |
| Beetle 80 (grams) | 1.50 | 1.50 | 1.50 | 0.94 | 0.94 |
| Jeffamine 1000M (grams) | 0.08 | 0.08 | 0.08 | 0.10 | 0.21 |
| Petro BAF (grams) | 0.05 | 0.05 | 0.05 | 0.05 | 0.05 |
| Lomar D (grams) | 1.10 | 0.50 | 0.25 | 1.00 | 1.00 |
| Water (grams) | 33.85 | 34.55 | 34.70 | 33.95 | 33.95 |

Example 27

Incorporation of an anionic mercaptoalkane carboxylate modifier into the walls of aminoplast microcapsules using Process (1) above in the presence of a colloid stabiliser.

A solution of Beetle 80 (5.0 g), 3-mercaptopropionic acid (0.14 g) and trichloroacetic acid (0.05 g) in Solvesso 200 (60.0 g) was heated at 50° C. for 3 hours. Q43 (0.31 g) was added to a portion of the Beetle 80 solution (12.19 g) and the resulting oil was emulsified into an aqueous phase comprising PetroBAF (0.06 g, 0.5% to oil) and Gohsenol GLO3 (1.0 g of a 25% aq. solution) in water (total mass 37.5 g, 25% solids) using a Silverson mixer at 7.5 Krpm for 2 min. The emulsion, with droplets of 5.3 ?m in diameter, was heated at 50° C. for 3 hours to give microcapsules of similar diameter.

Example 28

Incorporation of an aromatic sulphonate modifier into the walls of aminoplast microcapsules using Process (1) above. This experiment demonstrated that 2-sulfobenzoic acid cyclic anhydride can be reacted with an alkylated urea-formaldehyde resin using Process 1 to give a surface-active intermediate that could be incorporated into the walls of aminoplast microcapsules in the presence of a colloid stabiliser.

Beetle 80 (5.0 g) was added to a solution of 2-sulfobenzoic acid cyclic anhydride (0.15 g or 0.30 g, 3 or 6 mol % w.r.t U—F repeat units) in acetophenone (60.0 g) along with anhydrous triethylamine (0.11 mL). The solution was heated to 50° C. for 3 hours at which time no peaks due to cyclic anhydride could be seen in the IR spectrum.

Q43 (0.31 g or 0.15 g) was added to a portion of the Beetle 80 solution (12.19 g) in which 6% of U—F units had been reacted with 2-sulfobenzoic acid cyclic anhydride. This organic phase was emulsified using a Silverson mixer at 7.5 Krpm for 1 min into water at pH 2.8-3.0. Gohsenol GLO3

(2% on oil) and optionally PetroBAF (0.5% on oil) were either dissolved in the water before emulsification, or were added to the aqueous phase after emulsification such that the entire aqueous phase was 37.5 g (25% wt/wt internal phase). The emulsion was heated at 50° C. for 3 hours to give microcapsules. No wall formation occurred when PetroBAF was omitted from the emulsion.

The modified U—F resins were shown to be surface active as follows. A sample (4.0 g) of the above solutions was separately emulsified into water (6.0 g) using an Ystral mixer at 2 Krpm for 2 min. The 3% modified resin stabilised the emulsion for >1 hour at pH 10.5 but not at pH 2.2. The 6% modified resin stabilised the emulsion, having a PSD (D[v, 0.5]) of 2.0 ?m, for >1 hour at pH 3.0. Emulsions at pH 3.0 prepared from a 10 wt/wt % solution of unmodified Beetle 80 (not reacted with 2-sulfobenzoic acid cyclic anhydride) in acetophenone were unstable. Similarly unstable were emulsions of the same unmodified Beetle 80 solution in water containing 2-sulfobenzoic acid (the hydrolysis product of the cyclic anhydride) at an amount corresponding to that used in the modification reaction. This shows that the surface activity exhibited by the 6% modified U—F resin is not due to inherent surface activity of the resin itself, or of a hydrolysis product of the cyclic anhydride, or of the cyclic anhydride itself which is quickly hydrolysed during emulsification into acidic water.

Example 29

Incorporation of an anionic mercaptoalkane sulphonate modifier into the walls of aminoplast microcapsules containing lambda-cyhalothrin using Process (3) above. This experiment demonstrated that an anionic mercaptoalkane sulphonate could be built into aminoplast capsule walls.

2-Mercaptoethanesulphonic acid sodium salt is commercially available from Aldrich, and abbreviated here as "MESNA". An organic phase was prepared by dissolving lambda-cyhalothrin (5 g), Beetle 1050-10 (2.025 g) and pentaerythritol tetrakis 3-mercaptopropionate (0.22 g, Q43) in Solvesso 200 (15.25 g). This oil was emulsified into a solution of Gohsenol GLO3 (0.5 g) in water (25.45 g) using a Silverson stirrer, then Petro BAF (0.05 g) and a 50% aqueous solution of MESNA (0.5 g) were added. The pH of the emulsion was reduced to 2.8 by the drop wise addition of sulphuric acid (10:1 aqueous solution), and then the emulsion was paddle stirred at 55° C. for 3 hours. Finally the pH of the capsule suspension was adjusted to 6.5 by the drop wise addition of ammonia (1:1 aqueous solution). This resulted in 5.7 μm microcapsules which maintained their integrity upon drying, and which had a zeta potential of −21.1+/−2.8 mV (compared to a zeta potential of −12.4+/−2.0 mV for equivalent microcapsules from which the modifier was omitted).

Example 30

Incorporation of a cationic quaternary ammonium alkylamine into the walls of aminoplast microcapsules containing lambda-cyhalothrin using Process (3) above. This experiment demonstrated that a cationic quaternary ammonium alkylamine modifier could be built into aminoplast capsule walls.

An organic phase was prepared by dissolving lambda-cyhalothrin (5 g), Beetle 1050-10 (2.025 g) and pentaerythritol tetrakis 3-mercaptopropionate (0.225 g, Q43) in Solvesso 200 (15.25 g). This oil was emulsified into a solution of Gohsenol GLO3 (0.25 g), Petro BAF (0.05 g) and (2-aminoethyl)trimethylammonium chloride hydrochloride (0.55 g) in water (26.4 g) using a Silverson mixer. The pH of the emulsion was reduced to 1.9 by dropwise addition of sulphuric acid (10:1 aqueous solution), and then the emulsion was paddle stirred at 55° C. for 3 hours. Finally the pH of the capsule suspension was adjusted to 5.7 by the drop wise addition of ammonia (1:1 aqueous solution). This resulted in 7.9 μm microcapsules which maintained their integrity upon drying, and which had a zeta potential of −1.3+/−2.2 mV (compared to a zeta potential of −12.4+/−2.0 mV for equivalent microcapsules from which the modifier was omitted).

Although this invention has been described with respect to specific embodiments, the details hereof are not to be construed as limitations, for it will be apparent that various, equivalents, changes and modifications may be resorted to without parting from the spirit and scope of the invention, and it is understood that such equivalent embodiments are intended to be included within the scope of the invention.

What is claimed is:

1. A microcapsule comprising an encapsulated liquid enclosed within a solid permeable shell of a polymer resin wherein said polymer resin is made by the polymerisation of a urea formaldehyde prepolymer, in which the methylol (—CH$_2$OH) groups have optionally been partially etherified by reaction with a C$_4$-C$_{10}$ alkanol, and the polymer resin has incorporated therein at least one surface modifying compound having a moiety —X as defined below which reacts with the methylol or etherified methylol moieties in the urea formaldehyde prepolymer;

and wherein said surface modifying compound is of formula (IA), (IB), (IC), (ID), (IIA), (IIB), (IIC), (IIIA), (IIIB), (IIIC), (IIID) or (IVA) or is a sulfonate polyester polyol $$X—Y_1—Z \qquad \text{(IA)}$$

$$R_4—O(PO)_r(EO)_s—X \qquad \text{(IB)}$$

$$R_4'—(PO)_r(EO)_s(PO)_t—X \qquad \text{(IC)}$$

(ID)

$$X-(EO)_a(PO)_b—X' \qquad \text{(IIA)}$$

$$X—(PO)_a(EO)_b(PO)_c—X' \qquad \text{(IIB)}$$

(IIC)

$$X—Y_4'—\overset{\underset{R_{14}}{|}}{\overset{R_{15}}{\underset{|}{N^+}}}—Y_4—X \; A^-$$

$$X—Y_2—C(Z)(R_6)—Y_2'—X' \qquad \text{(IIIA)}$$

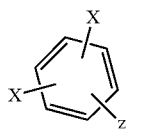

(IIIB)

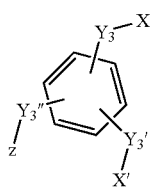

(IIIC)

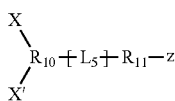

(IIID)

X—Y—NH—Y'—Z  (IVA)

wherein the sulfonate polyester polyol is prepared by reacting sodium sulphoisophthalic acid, adipic acid, cyclohexane dimethanol, methoxy-polyethylene glycol (MW 750) and trimethylol propane to give a product having a hydroxyl number in the range of from 150 to 170;

and wherein in formulae (IA), (IB), (IC), (IIA), (IIB), (IIC), (IIIA), (IIIB), (IIIC), (IIID) and (IVA) above; Z if present is sulphonate, carboxylate, phosphonate, phosphate, quaternary ammonium, betaine, oxyethylene or an oxyethylene-containing polymer;

and wherein in formulae (ID) above Z is sulphonate, phosphonate, phosphate, quaternary ammonium, betaine, oxyethylene or an oxyethylene-containing polymer;

and each X or X' is, independently, hydroxyl, thiol, a group —NHA wherein A is hydrogen or $C_1$ to $C_4$ alkyl, or a group —CO—OR where R is hydrogen or a hydrocarbyl moiety having 1-30 carbon atoms optionally linked or substituted by one or more halo, amino, ether or thioether groups or combinations of these;

and wherein in formula (IA) $Y_1$ is a moiety linking X and Z and is a straight or branched alkyl chain containing from 1 to 20 carbon atoms or is naphthyl, cyclopentyl or cyclohexyl;

and wherein in formula (IB) $R_4$ is an end-capping group which is $C_1$ to $C_4$ alkyl, r and s are independently from 0 to 3000, provided that s is not 0 and the total of r+s is from 7 to 3000, and EO and PO represent oxyethylene and oxypropylene respectively which may be arranged in random or block formation;

and wherein in formula (IC) $R_4'$ is an end-capping group which is $C_1$ to $C_4$ alkyl, r', s' and t are, independently, from 0 to 2000, provided that s' is not 0 and the total of r'+s'+t is from 7 to 3000, and EO and PO represent oxyethylene and oxypropylene respectively;

and wherein formula (ID) X and Z are as defined above; or X and Z are adjacent substituents which together with the carbon atom to which they are bound form a cyclic anhydride capable of ring-opening;

and wherein in formula (IIA) a and b are independently from 0 to 3000, provided that a is not 0 and the total of a+b is from 7 to 3000, and EO and PO represent oxyethylene and oxypropylene respectively which may be arranged in random or block formation;

and wherein in formula (IIB) a', b' and c are, independently, from 0 to 2000, provided that b' is not 0 and the total of a'+b'+c is from 7 to 3000, and EO and PO represent oxyethylene and oxypropylene respectively;

and wherein in formula (IIC) $R_{14}$ and $R_{15}$, which may be the same or different, are hydrogen, $C_1$ to $C_{20}$ straight or branched chain alkyl, aryl or $C_1$ to $C_4$ aralkyl, wherein each aryl group may be optionally substituted by $C_1$ to $C_4$ alkyl, nitro or halo, and $Y_4$ and $Y_4'$ which may be the same or different are —$R_8$— or —$R_7$-$(L_1)_n$- wherein $R_7$ and $R_8$ are, independently, $C_1$ to $C_{10}$ straight or branched chain alkyl linking groups optionally substituted by halogen or $C_1$ to $C_4$ alkoxy and $(L_1)_n$ is a polyoxyalkyene group wherein n is from 2 to 20 and A- is a suitable anion;

and wherein in formula (IIIA) $R_6$ is hydrogen or a $C_1$ to $C_4$ alkyl group optionally substituted by ether or halogen and $Y_2$ and $Y_2'$, which may be same or different, are independently —$R_7$-$(L_1)_n$- or —$R_8$ wherein $R_7$ and $R_8$ are, independently, $C_1$ to $C_{10}$ straight or branched chain alkyl linking groups optionally substituted by halogen or $C_1$ to $C_4$ alkoxy and $(L_1)_n$ is polyoxyethylene, polyoxypropylene or polyoxybutylene where n is from 2 to 20;

and wherein in formula (IIIB) X and Z are as previously defined;

and wherein in formula (IIIC) $Y_3$, $Y_3'$ and $Y_3''$ individually represent a direct link between X or Z (as the case may be) and the ring structure or may be a group

-$(L_2)$-$R_9$— where $L_2$ is an ester linking group —C(O)—O— and $R_9$ is oxyethylene, oxypropylene or oxybutylene or polyoxyethylene, polyoxypropylene or polyoxybutylene having a degree of polymerisation from 2 to 20;

and wherein in formula (IIID) $R_{10}$ is a $C_1$ to $C_8$ straight or branched chain alkyl group, the two groups X and X', which may be the same or different, may be attached to the same carbon atom in the alkyl chain or to different carbon atoms in the alkyl chain, -$L_5$- is a linking group which is -$(L_1)_n$- or —$R_8$— wherein $R_8$ and $(L_1)_n$ are as defined above in relation to formula (IIIA) and $R_{11}$ is $C_1$ to $C_4$ alkyl;

and wherein in formula (IVA) Y and Y' are each, independently, a straight or branched chain $C_1$ to $C_{10}$ alkyl group, a polyoxyethylene, polyoxypropylene or polyoxybutylene polymer chain of formula -$(L_1)_n$- as defined above or a group -$(L_2)$—$R_9$— as defined above.

2. A microcapsule according to claim 1 wherein when —Z is sulphonate, carboxylate, phosphonate or phosphate it is present as a salt providing the —$Z^-$ anion; or when —Z is quaternary ammonium it has the structure

[—$NR_1R_2R_3$]$^+$$A'^-$ wherein $R_1$, $R_2$ and $R_3$ are independently hydrogen or $C_1$ to $C_4$ alkyl and $A'^-$ is a suitable inorganic or organic anion, provided that not more than one of $R_1$, $R_2$ and $R_3$ is hydrogen; or when —Z is oxyetheylene or an oxyethylene-containing polymer, it is an oxyethylene polymer or is a random or block oxyethylene/oxypropylene copolymer containing an oxyethylene to oxypropylene ratio of greater than 1.

3. A microcapsule according to claim 1 wherein the polymer resin is made by the polymerisation of a urea formaldehyde prepolymer and the mole ratio of the surface modifying agent to the number of urea-formaldehyde repeat units in the urea formaldehyde prepolymer is between 1:40 to 1:4.

4. A microcapsule according to claim 1 wherein the encapsulated liquid comprises an agrochemical, an ink, a dye, a biologically active material or a pharmaceutical.

5. A modified process for the encapsulation of a liquid within a solid permeable shell of a polymer resin formed by polymerisation of a wall-forming material which comprises
making said polymer resin by the polymerisation of a urea formaldehyde prepolymer in which the methylol (—CH$_2$OH) groups have optionally been partially etherified by reaction with a C$_4$-C$_{10}$ alkanol, incorporating therein at least one surface modifying compound having a moiety —X which reacts with the methylol or etherified methylol moieties in the urea formaldehyde prepolymer;
wherein said surface modifying compound is of formula (IA), (IB), (IC), (ID), (IIA), (IIB), (IIC), (IIIA), (IIIB), (IIIC), (IIID) or (IVA) or is a sulfonate polyester polyol $$X—Y_1—Z \quad\quad (IA)$$

$$R_4—O(PO)_r(EO)_s—X \quad\quad (IB)$$

$$R_4'—O(PO)_r(EO)_s(PO)_t—X \quad\quad (IC)$$

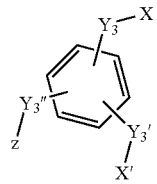
(ID)

$$X\text{-}(EO)_a(PO)_b—X' \quad\quad (IIA)$$

$$X—(PO)_a(EO)_b(PO)_cX' \quad\quad (IIB)$$

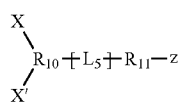
(IIC)

$$X—Y_2—C(Z)(R_6)—Y_2'—X' \quad\quad (IIIA)$$

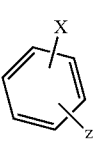
(IIIB)

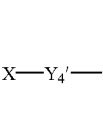
(IIIC)

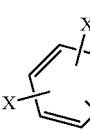
(IIID)

$$X—Y—NH—Y'—Z \quad\quad (IVA)$$

wherein the sulfonate polyester polyol is prepared by reacting sodium sulphoisophthalic acid, adipic acid, cyclohexane dimethanol, methoxy-polyethylene glycol (MW 750) and trimethylol propane to give a product having a hydroxyl number in the range of from 150 to 170;
and wherein in formulae (IA), (IB), (IC), (IIA), (IIB), (IIC), (IIIA), (IIIB), (IIIC), (IIID) and (IVA) above Z if present is sulphonate, carboxylate, phosphonate, phosphate, quaternary ammonium, betaine, oxyethylene or an oxyethylene-containing polymer;
and wherein in formulae (ID) above Z is sulphonate, phosphonate, phosphate, quaternary ammonium, betaine, oxyethylene or an oxyethylene-containing polymer;
and each X or X' is, independently, hydroxyl, thiol, a group —NHA wherein A is hydrogen or C$_1$ to C$_4$ alkyl, or a group —CO—OR where R is hydrogen or a hydrocarbyl moiety having 1-30 carbon atoms optionally linked or substituted by one or more halo, amino, ether or thioether groups or combinations of these;
and wherein in formula (IA) Y$_1$ is a moiety linking X and Z and is a straight or branched alkyl chain containing from 1 to 20 carbon atoms or is naphthyl, cyclopentyl or cyclohexyl;
and wherein in formula (IB) R$_4$ is an end-capping group which is C$_1$ to C$_4$ alkyl, r and s are independently from 0 to 3000, provided that s is not 0 and the total of r+s is from 7 to 3000, and EO and PO represent oxyethylene and oxypropylene respectively which may be arranged in random or block formation;
and wherein in formula (IC) R$_4$' is an end-capping group which is C$_1$ to C$_4$ alkyl, r', s' and t are, independently, from 0 to 2000, provided that s' is not 0 and the total of r'+s'+t is from 7 to 3000, and EO and PO represent oxyethylene and oxypropylene respectively;
and wherein formula (ID) X and Z are as defined above; or X and Z are adjacent substituents which together with the carbon atoms to which they are bound form a cyclic anhydride capable of ring-opening;
and wherein in formula (IIA) a and b are independently from 0 to 3000, provided that a is not 0 and the total of a+b is from 7 to 3000, and EO and PO represent oxyethylene and oxypropylene respectively which may be arranged in random or block formation;
and wherein in formula (IIB) a', b' and c are, independently, from 0 to 2000, provided that b' is not 0 and the total of a'+b'+c is from 7 to 3000, and EO and PO represent oxyethylene and oxypropylene respectively;

and wherein in formula (IIC) $R_{14}$ and $R_{15}$, which may be the same or different, are hydrogen, $C_1$ to $C_{20}$ straight or branched chain alkyl, aryl or $C_1$ to $C_4$ aralkyl, wherein each aryl group may be optionally substituted by $C_1$ to $C_4$ alkyl, nitro or halo, and $Y_4$ and $Y_4'$ which may be the same or different are —$R_8$— or —$R_7$-$(L_1)_n$- wherein $R_7$ and $R_8$ are, independently, $C_1$ to $C_{10}$ straight or branched chain alkyl linking groups optionally substituted by halogen or $C_1$ to $C_4$ alkoxy and $(L_1)_n$ is a polyoxyalkyene group wherein n is from 2 to 20 and A- is a suitable anion;

and wherein in formula (IIIA) $R_6$ is hydrogen or a $C_1$ to $C_4$ alkyl group optionally substituted by ether or halogen and $Y_2$ and $Y_2'$, which may be same or different, are independently —$R_7$-$(L_1)_n$- or —$R_8$— wherein $R_7$ and $R_8$ are, independently, $C_1$ to $C_{10}$ straight or branched chain alkyl linking groups optionally substituted by halogen or $C_1$ to $C_4$ alkoxy and $(L_1)_n$ is polyoxyethylene, polyoxypropylene or polyoxybutylene where n is from 2 to 20;

and wherein in formula (IIIB) X and Z are as previously defined;

and wherein in formula (IIIC) $Y_3$, $Y_3'$ and $Y_3''$ individually represent a direct link between X or Z (as the case may be) and the ring structure or may be a group

-$(L_2)$-$R_9$— where $L_2$ is an ester linking group —C(O)—O— and $R_9$ is oxyethylene, oxypropylene or oxybutylene or polyoxyethylene, polyoxypropylene or polyoxybutylene having a degree of polymerisation from 2 to 20;

and wherein in formula (IIID) $R_{10}$ is a $C_1$ to $C_8$ straight or branched chain alkyl group, the two groups X and X', which may be the same or different, may be attached to the same carbon atom in the alkyl chain or to different carbon atoms in the alkyl chain, -$L_5$- is a linking group which is -$(L_1)_n$- or —$R_8$— wherein $R_8$ and $(L_1)_n$ are as defined above in relation to formula (IIIA) and $R_{11}$ is $C_1$ to $C_4$ alkyl;

and wherein in formula (IVA) Y and Y' are each, independently, a straight or branched chain $C_1$ to $C_{10}$ alkyl group, a polyoxyethylene, polyoxypropylene or polyoxybutylene polymer chain of formula -$(L_1)_n$- as defined above or a group -$(L_2)$-$R_9$— as defined above.

6. A process according to claim 5 comprising
(a) reacting the surface-modifying compound with a urea formaldehyde prepolymer thereby forming a modified surface-active intermediate;
(b) preparing an organic solution or oil phase comprising the matcrial liquid to be encapsulated, the modified surface-active intermediate, and;
(c) creating an emulsion of the organic solution in a continuous phase aqueous solution comprising water and, optionally, a protective colloid, wherein the emulsion comprises discrete droplets of the organic solution dispersed throughout the continuous phase aqueous solution, with an interface formed between the discrete droplets of organic solution and the aqueous solution; and either
(d) causing in situ polymerization and/or curing of the modified prepolymer in the organic solution of the discrete droplets at the interface with the aqueous solution by heating the emulsion for a sufficient period of time and optionally adjusting the pH to a suitable value to allow substantial completion of wall formation, thereby converting the organic solution droplets to capsules consisting of solid, permeable, polymer shells enclosing the material and having the surface modifying compound incorporated therein; or as an alternative to (d)
(e) causing polymerization at the oil-water interface by bringing together a prepolymer added through the aqueous continuous phase and capable of reacting with the wall forming material(s) in the discontinuous oil phase.

7. A process according to claim 5 comprising
(a) preparing an organic solution or oil phase comprising the material to be encapsulated, the surface modifying compound and the wall-forming material;
(b) creating an emulsion of the organic solution in a continuous phase aqueous solution comprising water and, optionally, a protective colloid, wherein the emulsion comprises discrete droplets of the organic solution dispersed throughout the continuous phase aqueous solution, with an interface formed between the discrete droplets of organic solution and the aqueous solution; and either
(c) causing in situ polymerization and/or curing of the modified wall-forming material in the organic solution of the discrete droplets at the interface with the aqueous solution by heating the emulsion for a sufficient period of time and optionally adjusting the pH to a suitable value to allow substantial completion of wall formation, thereby converting the organic solution droplets to capsules consisting of solid, permeable, modified polymer shells enclosing the material; or as an alternative to (c)
(d) causing polymerization at the oil-water interface by bringing together a wall forming material added through the aqueous continuous phase and capable of reacting with the wall forming material(s) in the discontinuous oil phase.

8. A process according to claim 5 comprising
(a) preparing an organic solution or oil phase comprising the liquid to be encapsulated and the urea-formaldehyde prepolymer;
(b) creating an emulsion of the organic solution in a continuous phase aqueous solution comprising water and the surface-modifying compound(s), wherein the emulsion comprises discrete droplets of the organic solution dispersed throughout the continuous phase aqueous solution, with an interface formed between the discrete droplets of organic solution and the aqueous solution; and
(c) causing in situ polymerization and/or curing of the urea-formaldehyde prepolymer so that the surface-modifying molecule(s) is incorporated into the wall by heating the emulsion for a sufficient period of time and optionally adjusting the pH to a suitable value, to allow substantial completion of wall formation, thereby converting the organic solution droplets to capsules consisting of solid, permeable, modified polymer shells enclosing the liquid.

9. A process according to claim 5 comprising
(a) preparing an organic solution or oil phase comprising the material to be encapsulated and a first wall-forming material(s);
(b) creating an emulsion of the organic solution in a continuous phase aqueous solution comprising water and the surface-modifying compound(s), wherein the emulsion comprises discrete droplets of the organic solution dispersed throughout the continuous phase aqueous solution, with an interface formed between the discrete droplets of organic solution and the aqueous solution whereupon the surface modifying compounds(s) react at the interface with wall forming material from the organic phase; and (c) causing polymerization at the oil-water interface by bringing together a second wall forming material added through the aqueous continuous phase and capable of reacting with the first wall forming material(s) in the discontinuous oil phase.

10. A process according to claim 5 wherein there is employed a combination of the processes selected from at least two of the following:

1) a process comprising
   a) reacting the surface-modifying compound with at least one wall-forming material thereby forming a modified surface-active intermediate;
   b) preparing an organic solution or oil phase comprising the material to be encapsulated, the modified surface-active intermediate, and, optionally, additional wall-forming material;
   c) creating an emulsion of the organic solution in a continuous phase aqueous solution comprising water and, optionally, a protective colloid, wherein the emulsion comprises discrete droplets of the organic solution dispersed throughout the continuous phase aqueous solution, with an interface formed between the discrete droplets of organic solution and the aqueous solution; and either
   d) causing in situ polymerization and/or curing of the modified wall-forming material in the organic solution of the discrete droplets at the interface with the aqueous solution by heating the emulsion for a sufficient period of time and optionally adjusting the pH to a suitable value to allow substantial completion of wall formation, thereby converting the organic solution droplets to capsules consisting of solid, permeable, polymer shells enclosing the material and having the surface modifying compound incorporated therein, or as an alternative to (d)
   e) causing polymerization at the oil-water interface by bringing together a wall forming material added through the aqueous continuous phase and capable of reacting with the wall forming material(s) in the discontinuous oil phase;

2) a process comprising
   a) preparing an organic solution or oil phase comprising the material to be encapsulated, the surface modifying compound and the wall-forming material
   b) creating an emulsion of the organic solution in a continuous phase aqueous solution comprising water and, optionally, a protective colloid, wherein the emulsion comprises discrete droplets of the organic solution dispersed throughout the continuous phase aqueous solution, with an interface formed between the discrete droplets of organic solution and the aqueous solution; and either
   c) causing in situ polymerization and/or curing of the modified wall-forming material in the organic solution of the discrete droplets at the interface with the aqueous solution by heating the emulsion for a sufficient period of time and optionally adjusting the pH to a suitable value to allow substantial completion of wall formation, thereby converting the organic solution droplets to capsules consisting of solid, permeable, modified polymer shells enclosing the material; or as an alternative to (c)
   d) causing polymerization at the oil-water interface by bringing together a wall forming material added through the aqueous continuous phase and capable of reacting with the wall forming material(s) in the discontinuous oil phase;

3) a process comprising
   a) preparing an organic solution or oil phase comprising the material to be encapsulated and the wall-forming material;
   b) creating an emulsion of the organic solution in a continuous phase aqueous solution comprising water and the surface-modifying compound(s), wherein the emulsion comprises discrete droplets of the organic solution dispersed throughout the continuous phase aqueous solution, with an interface formed between the discrete droplets of organic solution and the aqueous solution; and
   c) causing in situ polymerization and/or curing of the wall-forming material so that the surface-modifying molecule(s) is incorporated into the wall by heating the emulsion for a sufficient period of time and optionally adjusting the pH to a suitable value, to allow substantial completion of wall formation, thereby converting the organic solution droplets to capsules consisting of solid, permeable, modified polymer shells enclosing the material; and 4) a process comprising
   a) preparing an organic solution or oil phase comprising the material to be encapsulated and a first wall-forming material(s);
   b) creating an emulsion of the organic solution in a continuous phase aqueous solution comprising water and the surface-modifying compound(s), wherein the emulsion comprises discrete droplets of the organic solution dispersed throughout the continuous phase aqueous solution, with an interface formed between the discrete droplets of organic solution and the aqueous solution whereupon the surface modifying compounds(s) react at the interface with wall forming material from the organic phase; and
   c) causing polymerization at the oil-water interface by bringing together a second wall forming material added through the aqueous continuous phase and capable of reacting with the first wall forming material(s) in the discontinuous oil phase.

11. A process according to claim 5 wherein the encapsulated liquid comprises an agrochemical, an ink, a dye, a biologically active material or a pharmaceutical.

12. A method for modifying the soil mobility of an agrochemical, comprising:
  (a) encapsulating the agrochemical within a solid permeable shell of a polymer resin wherein:
    said polymer resin is made by the polymerisation of a urea formaldehyde prepolymer in which the methylol ($-CH_2OH$) groups have optionally been partially etherified by reaction with a $C_4$-$C_{10}$ alkanol, incorporating therein at least one surface modifying compound having a moiety $-X$ which reacts with the methylol or etherified methylol moieties in the urea formaldehyde prepolymer;
    wherein said surface modifying compound is of formula (IA), (IB), (IC), (ID), (IIA), (IIB), (IIC), (IIIA), (IIIB), (IIIC), (IIID) or (IVA) or is a sulfonate polyester polyol

X—Y₁—Z (IA)

R₄—O(PO)ᵣ(EO)ₛ—X (IB)

R₄'—O(PO)ᵣ'(EO)ₛ'(PO)ₜ—X (IC)

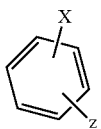
(ID)

X-(EO)ₐ(PO)ᵦ—X' (IIA)

X—(PO)ₐ'(EO)ᵦ'(PO)ᵧ—X' (IIB)

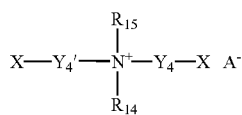
(IIC)

X—Y₂—C(Z)(R₆)—Y₂'—X' (IIIA)

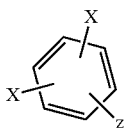
(IIIB)

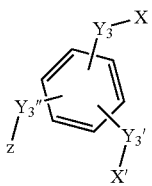
(IIIC)

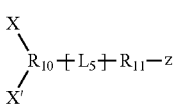
(IIID)

X—Y—NH—Y'—Z (IVA)

wherein the sulfonate polyester polyol is prepared by reacting sodium sulphoisophthalic acid, adipic acid, cyclohexane dimethanol, methoxy-polyethylene glycol (MW 750) and trimethylol propane to give a product having a hydroxyl number in the range of from 150 to 170;

and wherein in formulae (IA), (IB), (IC), (IIA), (IIB), (IIC), (IIIA), (IIIB), (IIIC), (IIID) and (IVA) above Z if present is sulphonate, carboxylate, phosphonate, phosphate, quaternary ammonium, betaine, oxyethylene or an oxyethylene-containing polymer;

and wherein in formulae (ID) above Z is sulphonate, phosphonate, phosphate, quaternary ammonium, betaine, oxyethylene or an oxyethylene-containing polymer;

and each X or X' is, independently, hydroxyl, thiol, a group —NHA wherein A is hydrogen or $C_1$ to $C_4$ alkyl, or a group —CO—OR where R is hydrogen or a hydrocarbyl moiety having 1-30 carbon atoms optionally linked or substituted by one or more halo, amino, ether or thioether groups or combinations of these;

and wherein in formula (IA) $Y_1$ is a moiety linking X and Z and is a straight or branched alkyl chain containing from 1 to 20 carbon atoms or is naphthyl, cyclopentyl or cyclohexyl;

and wherein in formula (IB) $R_4$ is an end-capping group which is $C_1$ to $C_4$ alkyl, r and s are independently from 0 to 3000, provided that s is not 0 and the total of r+s is from 7 to 3000, and EO and PO represent oxyethylene and oxypropylene respectively which may be arranged in random or block formation;

and wherein in formula (IC) $R_4'$ is an end-capping group which is $C_1$ to $C_4$ alkyl, r', s' and t are, independently, from 0 to 2000, provided that s' is not 0 and the total of r'+s'+t is from 7 to 3000, and EO and PO represent oxyethylene and oxypropylene respectively;

and wherein formula (ID) X and Z are as defined above; or X and Z are adjacent substituents which together with the carbon atoms to which they are bound form a cyclic anhydride capable of ring-opening;

and wherein in formula (IIA) a and b are independently from 0 to 3000, provided that a is not 0 and the total of a+b is from 7 to 3000, and EO and PO represent oxyethylene and oxypropylene respectively which may be arranged in random or block formation;

and wherein in formula (IIB) a', b' and c are, independently, from 0 to 2000, provided that b' is not 0 and the total of a'+b'+c is from 7 to 3000, and EO and PO represent oxyethylene and oxypropylene respectively;

and wherein in formula (IIC) $R_{14}$ and $R_{15}$, which may be the same or different, are hydrogen, $C_1$ to $C_{20}$ straight or branched chain alkyl, aryl or $C_1$ to $C_4$ aralkyl, wherein each aryl group may be optionally substituted by $C_1$ to $C_4$ alkyl, nitro or halo, and $Y_4$ and $Y_4'$ which may be the same or different are —R₈— or —R₇-(L₁)ₙ- wherein $R_7$ and $R_8$ are, independently, $C_1$ to $C_{10}$ straight or branched chain alkyl linking groups optionally substituted by halogen or $C_1$ to $C_4$ alkoxy and $(L_1)_n$ is a polyoxyalkyene group wherein n is from 2 to 20 and A- is a suitable anion;

and wherein in formula (IIIA) $R_6$ is hydrogen or a $C_1$ to $C_4$ alkyl group optionally substituted by ether or halogen and $Y_2$ and $Y_2'$, which may be same or different, are independently —R₇-(L₁)ₙ- or —R₈— wherein $R_7$ and $R_8$ are, independently, $C_1$ to $C_{10}$ straight or branched chain alkyl linking groups optionally substituted by halogen or $C_1$ to $C_4$ alkoxy and $(L_1)_n$ is polyoxyethylene, polyoxypropylene or polyoxybutylene where n is from 2 to 20;

and wherein in formula (IIIB) X and Z are as previously defined;

and wherein in formula (IIIC) $Y_3$, $Y_3'$ and $Y_3''$ individually represent a direct link between X or Z (as the case may be) and the ring structure or may be a group

-(L₂)-R₉— where $L_2$ is an ester linking group —C(O)—O— and $R_9$ is oxyethylene, oxypropylene or oxybutylene or polyoxyethylene, polyoxypropylene or polyoxybutylene having a degree of polymerisation from 2 to 20;

and wherein in formula (IIID) $R_{10}$ is a $C_1$ to $C_8$ straight or branched chain alkyl group, the two groups X and X', which may be the same or different, may be attached to the same carbon atom in the alkyl chain or to different carbon atoms in the alkyl chain, $-L_5-$ is a linking group which is $-(L_1)_n-$ or $—R_8—$ wherein $R_8$ and $(L_1)_n$ are as defined above in relation to formula (IIIA) and $R_{11}$ is $C_1$ to $C_4$ alkyl;

and wherein in formula (IVA) Y and Y' are each, independently, a straight or branched chain $C_1$ to $C_{10}$ alkyl group, a polyoxyethylene, polyoxypropylene or polyoxybutylene polymer chain of formula $-(L_1)_n-$ as defined above or a group $-(L_2)—R_9—$ as defined above; and (b) applying the encapsulated agrochemical to soil.

* * * * *